US009877997B2

(12) United States Patent
Wilson et al.

(10) Patent No.: US 9,877,997 B2
(45) Date of Patent: Jan. 30, 2018

(54) METHODS AND COMPOSITIONS FOR REGULATING SRCA2A EXPRESSION LEVELS IN MYOCARDIAL INFARCTION

(71) Applicant: Stealth BioTherapeutics Corp., Monaco (MC)

(72) Inventors: D. Travis Wilson, Newton, MA (US); Robert A. Kloner, Toluca Lake, CA (US)

(73) Assignee: Stealth BioTherapeutics Corp, Monaco (MC)

( * ) Notice: Subject to any disclaimer, the term of this patent is extended or adjusted under 35 U.S.C. 154(b) by 0 days.

(21) Appl. No.: 14/899,007

(22) PCT Filed: Jun. 24, 2014

(86) PCT No.: PCT/US2014/043929
§ 371 (c)(1),
(2) Date: Dec. 16, 2015

(87) PCT Pub. No.: WO2015/009414
PCT Pub. Date: Jan. 22, 2015

(65) Prior Publication Data
US 2016/0120931 A1 May 5, 2016

Related U.S. Application Data

(60) Provisional application No. 61/839,758, filed on Jun. 26, 2013.

(51) Int. Cl.
| | | |
|---|---|---|
| *A61K 38/07* | (2006.01) | |
| *A61K 38/06* | (2006.01) | |
| *A61K 45/06* | (2006.01) | |
| *A61K 31/401* | (2006.01) | |
| *A61K 31/573* | (2006.01) | |

(52) U.S. Cl.
CPC ............ *A61K 38/06* (2013.01); *A61K 31/401* (2013.01); *A61K 31/573* (2013.01); *A61K 38/07* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,522,811 | A | 6/1985 | Eppstein et al. |
| 5,674,534 | A | 10/1997 | Zale et al. |
| 5,716,644 | A | 2/1998 | Zale et al. |
| 6,468,798 | B1 | 10/2002 | Debs et al. |
| 6,900,178 | B2 | 5/2005 | Oeltgen et al. |

FOREIGN PATENT DOCUMENTS

| | | |
|---|---|---|
| WO | WO-96/40073 | 12/1996 |
| WO | WO-99/15154 | 4/1999 |
| WO | WO-2011/082324 A1 | 7/2011 |

OTHER PUBLICATIONS

Chonn, Arcadio et al., "Recent Advances in Liposomal Drug-Delivery Systems," Current Opinion in Biotechnology, (1995), vol. 6, pp. 698-708.
International Search Report and Written Opinion of the International Searching Authority for Application No. PCT/US2014/043929 dated Nov. 4, 2014, 8 pages.
Kawase, Yoshiaki et al., "Reversal of Cardiac Dysfunction After Long-Term Expression of SERCA2a by Gene Transfer in a Pre-Clinical Model of Heart Failure," J. American College of Cardiology, (Mar. 18, 2008), vol. 51, No. 11, pp. 1112-1119.
Kozarich, John W. et al., "Next generation therapeutics: Looking to the horizon: Editorial overview," Current Opinion in Chemical Biology, (1998), vol. 2, Issue 4, pp. 439-440.
Li, Yapeng et al., "Fasudil Protects the Heart against Ischemia-Reperfusion Injury by Attenuating Endoplasmic Reticulum Stress and Modulating SERCA Activity: The Differential Role for PI3K/Akt and JAK2/STAT3 Signaling Pathways," PLoS One, (Oct. 31, 2012), vol. 7, No. 10, pp. e48115, 12 pages.
Lichtenberg, Dov et al., "Liposomes: Preparation, Characterization, and Preservation," Methods Biochem. Anal., (1998), vol. 33, pp. 337-462.
Mizuguchi, Hiroyuki et al., "Intratumor administration of fusogenic liposomes containing fragment A of diphtheria toxin suppresses tumor growth," Cancer Lett., (1996), vol. 100, Issue 1, pp. 63-69.
Niwano, Kazuo et al., "Lentiviral Vector-mediated SERCA2 Gene Transfer Protects Against Heart Failure and Left Ventricular Remodeling After Myocardial Infarction in Rats," Molecular Therapy, (Jun. 2008), vol. 16, No. 6, pp. 1026-1032.
Reddy, K. Rajender, "Controlled-Release, Pegylation, Liposomal Formulations: New Mechanisms in the Delivery of Injectable Drugs," Ann Pharmacother., (Jul./Aug. 2000), vol. 34, pp. 915-923.
Schwartz, Robert J. et al., "Weighing in on Heart Failure: The Role of SERCA2a SUMOylation," Circ. Res., (2002), vol. 100, pp. 198-199.
Seehase, Matthias et al., "Gene Expression of the Na+-Ca2+ Exchanger, SERCA2a and Calsequestrin after Myocardial Ischemia in the Neonatal Rabbit Heart," Biology of the Neonate, (Apr. 25, 2006), vol. 90, pp. 174-184.
Weiner, Alan L., "Liposomes for Protein Delivery: Selecting Manufacture and Development Processes," Immunomethods, (1994), 4(3), pp. 201-209.
Zarain-Herzberg, A. et al., "Decreased expression of cardiac sarcoplasmic reticulum Ca(2+)-pump ATPase in congestive heart failure due to myocardial infarction," Mol. Cell. Biochem., (Oct.-Nov. 1996), vols. 163-164, pp. 285-290.
Zhao, Kesheng et al., "Transcellular Transport of a Highly Polar 3+ Net Charge Opioid Tetrapeptide," Journal of Pharmacology and Experimental Therapeutics, (2003), vol. 304, No. 1, pp. 425-432.
Glick et al., Randomized evaluation of the effects of filter-based distal protection on myocardial perfusion and infarct size after primary percutaneous catheter intervention in myocardial infarction with and without ST-segment evaluation, Circul. 112:1462-1469 (2005).
Gregoriadis. "Engineering Liposomes for Drug Delivery: Progress and Problems," Trends in Biotechnology, (Dec. 1995), vol. 13, No. 12, pp. 527-537.

*Primary Examiner* — Julie Ha
*Assistant Examiner* — Kristina M Hellman
(74) *Attorney, Agent, or Firm* — Foley & Lardner LLP

(57) ABSTRACT

The disclosure provides methods and compositions for increasing SERCA2a expression levels in a mammalian subject in need thereof. The methods comprise administering to the subject a therapeutic amount of an aromatic-cationic peptide to subjects in need thereof. In some embodiments, the aromatic-cationic peptide is D-Arg-2'6'-Dmt-Lys-Phe-NH2, or a pharmaceutically acceptable salt thereof such as acetate or trifluoroacetate salt. In some embodiments, the subject has suffered a myocardial infarction.

10 Claims, 10 Drawing Sheets

D-Arg-2'6'-Dmt-Lys-Phe-NH$_2$

METHODS AND COMPOSITIONS FOR REGULATING SRCA2A EXPRESSION LEVELS IN MYOCARDIAL INFARCTION

CROSS-REFERENCE TO RELATED APPLICATIONS

This Application is a U.S. National Stage Application under 35 U.S.C. § 371 of International Application No. PCT/US2014/043929, filed on Jun. 24, 2014, which claims the benefit of and priority to U.S. Application No. 61/839,758, filed Jun. 26, 2013, which are incorporated herein by reference in their entireties.

TECHNICAL FIELD

The present technology relates generally to methods of treating or preventing left ventricular remodeling in a subject in need thereof. In particular, the present technology relates to administering aromatic-cationic peptides in effective amounts to regulate (e.g., increase) sarco/endoplasmic reticulum Ca2+-ATPase 2a ("SERCA2a") post myocardial infarction.

BACKGROUND

The following description is provided to assist the understanding of the reader. None of the information provided or references cited is admitted to be prior art to the present technology.

Following myocardial infarction there is a dynamic and progressive left ventricle (LV) remodeling that contributes to LV dilation, heart failure, and death. LV remodeling increases LV wall stress, which leads to an increase in oxygen demand. To help compensate for the loss of myocardium and reduced stroke volume, the LV develops global dilation and the non-infarcted wall of the LV develops eccentric hypertrophy. As the ventricle dilates, the dilation process initially helps to compensate for reduced stroke volume. However, eventually progressive dilatation and hypertrophy lead to congestive heart failure. One of the strongest predictors of death one year post myocardial infarction is the volume of the left ventricle.

SUMMARY

The present technology relates generally to the normalization (e.g., increase) of SERCA2a expression by administration of therapeutically effective amounts of aromatic-cationic peptides to subjects in need thereof.

In some aspects, the present technology provides methods for normalizing or stabilizing (e.g., increasing) SERCA2a expression a mammalian subject in need thereof by administering a therapeutically effective amount an aromatic-cationic peptide.

In some embodiments, the stabilization (e.g., increasing) of SERCA2a expression prevents, ameliorates, or treats LV remodeling.

In some embodiments, the aromatic-cationic peptide is D-Arg-2'6'-Dmt-Lys-Phe-NH$_2$, or a pharmaceutically acceptable salt thereof such as acetate or trifluoroacetate salt. In some embodiments, the subject has suffered a myocardial infarction.

DETAILED DESCRIPTION

Figure 1:
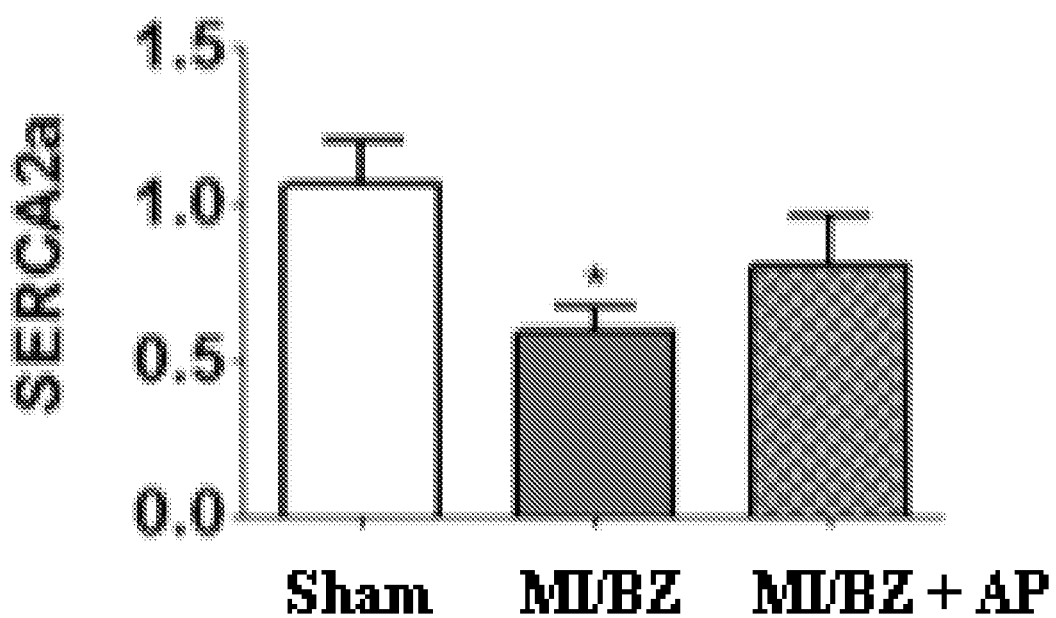
FIG. 1 is a graph showing the effect of D-Arg-2'6'-Dmt-Lys-Phe-NH$_2$ on SERCA2a expression in border zone cells and remote area cells.

It is to be appreciated that certain aspects, modes, embodiments, variations and features of the technology are described below in various levels of detail in order to provide a substantial understanding of the present technology. The definitions of certain terms as used in this specification are provided below. Unless defined otherwise, all technical and scientific terms used herein generally have the same meaning as commonly understood by one of ordinary skill in the art to which this technology belongs.

As used in this specification and the appended claims, the singular forms "a", "an" and "the" include plural referents unless the content clearly dictates otherwise. For example, reference to "a cell" includes a combination of two or more cells, and the like.

As used herein, the "administration" of an agent, drug, or peptide to a subject includes any route of introducing or delivering to a subject a compound to perform its intended function. Administration can be carried out by any suitable route, including orally, intranasally, parenterally (intravenously, intramuscularly, intraperitoneally, or subcutaneously), or topically. Administration includes self-administration and the administration by another.

As used herein, the term "amino acid" includes naturally-occurring amino acids and synthetic amino acids, as well as amino acid analogs and amino acid mimetics that function in a manner similar to the naturally-occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally-occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. Amino acids can be referred to herein by either their commonly known three letter symbols or by the one-letter symbols recommended by the IUPAC-IUB Biochemical Nomenclature Commission.

As used herein, the term "border zone cells" refers to cardiac cells that border, surround, or lie in close proximity to an infarct zone in a heart. In some embodiments, the border zone is a strip of non-infarcted heart tissue about 2 mm in width surrounding the scar. Border zone cells are the cardiac cells that are subject to left ventricular remodeling, as the border zone cells compensate for the necrotic cardiac tissue resulting from the infarct.

As used herein, the term "remote cells" refers to cardiac cells beyond the border zone cells. These cells lie farther away from the infarct zone and normally remain unaffected from the infarction.

As used herein, the term "control" has its customary meaning in the art, and can refer to e.g., cells, such as border zone cells or remote cells, that are not treated with a therapeutic agent or test agent, e.g., such an aromatic-cationic peptide. Controls can be used, as is known in the art, as "standards" to ascertain the effect of a particular treatment. For example, control (untreated) border zone cells and remote cells can be used to determine the effect of aromatic-cationic peptide treatment on border zone cells and remote cells.

As used herein, the term "effective amount" refers to a quantity sufficient to achieve a desired therapeutic and/or prophylactic effect, e.g., an amount that results in the stabilization (e.g., increase) of SERCA2a expression. Additionally, as used herein, effective amount can refer to a quantity that results in a prevention of, or a decrease in, LV remodeling or one or more symptoms associated with LV remodeling. In the context of therapeutic or prophylactic applications, the amount of a composition administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors.

As used herein, the term "left ventricle (LV) remodeling" has its customary meaning known in the art and refers to a condition typically characterized by increasing LV wall stress and increasing oxygen demand. LV remodeling may also include LV dilation and the development of eccentric hypertrophy in the non-infarct cardiac cells of the LV. During this process, sarcomeres are added on in a circumferential or lengthwise fashion. As the ventricle dilates this process initially helps to compensate for reduced stroke volume, but eventually progressive dilatation and hypertrophy lead to congestive heart failure. One of the strongest predictors of death one year post myocardial infarction is the volume of the left ventricle. The more dilated, the greater the chance of death. The signs of LV remodeling include, but are not limited to: reduced LV stroke volume, reduced LV ejection fraction, poor fractional shortening, increased infarct expansion, poor hemodynamics, increased scar formation in LV myocardium, and increased lung volumes.

An used herein, the terms "isolated" or "purified" polypeptide or peptide refers to polypeptides or peptides substantially free of cellular material or other contaminating polypeptides from the cell or tissue source from which the agent is derived, or substantially free from chemical precursors or other chemicals when chemically synthesized. For example, an isolated aromatic-cationic peptide would be free of materials that would interfere with diagnostic or therapeutic uses of the agent. Such interfering materials may include enzymes, hormones and other proteinaceous and nonproteinaceous solutes.

As used herein, "net charge" refers to the balance of the number of positive charges and the number of negative charges carried by the amino acids present in the peptide. In this specification, it is understood that net charges are measured at physiological pH. The naturally occurring amino acids that are positively charged at physiological pH include L-lysine, L-arginine, and L-histidine. The naturally occurring amino acids that are negatively charged at physiological pH include L-aspartic acid and L-glutamic acid.

As used herein, the term "pharmaceutically acceptable salt" refers a salt prepared from a base or an acid which is acceptable for administration to a patient, such as a mammal (e.g., salts having acceptable mammalian safety for a given dosage regime). However, it is understood that the salts are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. In addition, when a peptide contains both a basic moiety, such as an amine, pyridine or imidazole, and an acidic moiety such as a carboxylic acid or tetrazole, zwitterions may be formed and are included within the term "salt" as used herein.

As used herein the term "pharmaceutically acceptable carrier" includes saline, solvents, dispersion media, coatings, antibacterial and antifungal agents, isotonic and absorption delaying agents, and the like, compatible with pharmaceutical administration.

As used herein, the terms "polypeptide," "peptide," and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art.

As used herein, the term "simultaneous" therapeutic use refers to the administration of at least two active ingredients by the same route and at the same time or at substantially the same time.

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

As used herein, the term "stabilize" or "stabilizing" in regards to gene expression (e.g., SERCA2a expression) refers to maintaining, normalizing or regaining gene expression levels (e.g., RNA or protein levels) in cells, such as border zone or remote infarct cardiac cells, to about the same level of expression as non-infarct normal cardiac cells. For example, as disclosed herein, administration of an aromatic-cationic peptide to subjects with reduced SERCA2a levels results in the subject having increased SERCA2a levels as compared to untreated control subjects. In some embodiments, administration of an aromatic-cationic peptide to a subject susceptible to or suffering from a disease or condition characterized by low SERCA2a levels results in the subject having higher SERCA2a levels (e.g., less reduction in SERCA2a expression levels) than an untreated control subject.

As used herein, the terms "treating," "treatment," or "alleviation" refers to therapeutic treatment, wherein the object is to reduce or slow down (lessen) the targeted pathologic condition or disorder. For example, a subject is successfully "treated" for LV remodeling if, after receiving a therapeutic amount of the aromatic-cationic peptides according to the methods described herein, the subject shows observable and/or measurable reduction in or absence of (e.g., a physiological improvement of) one or more signs and symptoms of LV remodeling, such as, e.g., reduced LV stroke volume, reduced LV ejection fraction, poor fractional shortening, increased infarct expansion, poor hemodynamics, increased scar formation in LV myocardium, myocardial stretching and thinning, and increased lung volumes. It is also to be appreciated that the various modes of treatment or prevention of medical conditions as described are intended to mean "substantial," which includes total but also less than total treatment or prevention, and wherein some biologically or medically relevant result is achieved. Treating LV remodeling, as used herein, also refers to the increase or preventing the decease of mitochondrial biogenesis. In some embodiments, treating LV remodeling includes increasing expression levels of SERCA2a (e.g., RNA and/or protein levels) and/or activity in a subject in need thereof.

As used herein, "prevention" or "preventing" of a disorder or condition refers to a compound that, in a statistical sample, reduces the occurrence of the disorder or condition in the treated sample relative to an untreated control sample, or delays the onset of one or more symptoms of the disorder or condition relative to the untreated control sample. As used herein, preventing LV remodeling includes preventing the initiation of LV remodeling, delaying the initiation of LV remodeling, preventing the progression or advancement of LV remodeling, slowing the progression or advancement of LV remodeling, and delaying the progression or advancement of LV remodeling. In some embodiments, preventing LV remodeling includes increasing expression levels of SERCA2a (e.g., RNA and/or protein levels) and/or activity in a subject in need thereof.

As used herein, the term "chronic," with reference to administration, refers to administration of a therapeutic agent, such as an aromatic-cationic peptide, for about 3 days, about 4 days, about 5 days, about 6 days, about 1 week, about 2 weeks, about 3 weeks, 4 weeks, 5 weeks 6 weeks, about 2 months, about 3 months, about 6 months, about 9 months, about 1 year or longer. In some embodiments, chronic administration includes administration once per day, twice per day, 3-5 times per day, every other day, every third day, once per week or once per month.

Aromatic-Cationic Peptides

The present technology relates to the stabilization of SERCA2a expression and related conditions by administration of certain aromatic-cationic peptides. The aromatic-cationic peptides are water-soluble and highly polar. Despite these properties, the peptides can readily penetrate cell membranes. The aromatic-cationic peptides typically include a minimum of three amino acids or a minimum of four amino acids, covalently joined by peptide bonds. The maximum number of amino acids present in the aromatic-cationic peptides is about twenty amino acids covalently joined by peptide bonds. Suitably, the maximum number of amino acids is about twelve, more preferably about nine, and most preferably about six.

The amino acids of the aromatic-cationic peptides can be any amino acid. The amino acids may be naturally occurring. Naturally occurring amino acids include, for example, the twenty most common levorotatory (L) amino acids normally found in mammalian proteins, i.e., alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan, (Trp), tyrosine (Tyr), and valine (Val). Other naturally occurring amino acids include, for example, amino acids that are synthesized in metabolic processes not associated with protein synthesis. For example, the amino acids ornithine and citrulline are synthesized in mammalian metabolism during the production of urea. Another example of a naturally occurring amino acid includes hydroxyproline (Hyp).

The peptides optionally contain one or more non-naturally occurring amino acids. Optimally, the peptide has no amino acids that are naturally occurring. The non-naturally occurring amino acids may be levorotary (L-), dextrorotatory (D-), or mixtures thereof. Non-naturally occurring amino acids are those amino acids that typically are not synthesized in normal metabolic processes in living organisms, and do not naturally occur in proteins. In addition, the non-naturally occurring amino acids suitably are also not recognized by common proteases. The non-naturally occurring amino acid can be present at any position in the peptide. For example, the non-naturally occurring amino acid can be at the N-terminus, the C-terminus, or at any position between the N-terminus and the C-terminus.

The non-natural amino acids may, for example, comprise alkyl, aryl, or alkylaryl groups not found in natural amino acids. Some examples of non-natural alkyl amino acids include α-aminobutyric acid, β-aminobutyric acid, γ-aminobutyric acid, δ-aminovaleric acid, and ε-aminocaproic acid. Some examples of non-natural aryl amino acids include ortho-, meta, and para-aminobenzoic acid. Some examples of non-natural alkylaryl amino acids include ortho-, meta-, and para-aminophenylacetic acid, and γ-phenyl-β-aminobutyric acid. Non-naturally occurring amino acids include derivatives of naturally occurring amino acids. The derivatives of naturally occurring amino acids may, for example, include the addition of one or more chemical groups to the naturally occurring amino acid.

For example, one or more chemical groups can be added to one or more of the 2', 3', 4', 5', or 6' position of the aromatic ring of a phenylalanine or tyrosine residue, or the 4', 5', 6', or 7' position of the benzo ring of a tryptophan residue. The group can be any chemical group that can be added to an aromatic ring. Some examples of such groups include branched or unbranched $C_1$-$C_4$ alkyl, such as methyl, ethyl, n-propyl, isopropyl, butyl, isobutyl, or t-butyl, $C_1$-$C_4$ alkyloxy (i.e., alkoxy), amino, $C_1$-$C_4$ alkylamino and $C_1$-$C_4$ dialkylamino (e.g., methylamino, dimethylamino), nitro, hydroxyl, halo (i.e., fluoro, chloro, bromo, or iodo). Some specific examples of non-naturally occurring derivatives of naturally occurring amino acids include norvaline (Nva) and norleucine (Nle).

Another example of a modification of an amino acid in a peptide is the derivatization of a carboxyl group of an aspartic acid or a glutamic acid residue of the peptide. One example of derivatization is amidation with ammonia or with a primary or secondary amine, e.g., methylamine, ethylamine, dimethylamine or diethylamine. Another example of derivatization includes esterification with, for example, methyl or ethyl alcohol. Another such modification includes derivatization of an amino group of a lysine, arginine, or histidine residue. For example, such amino groups can be acylated. Some suitable acyl groups include, for example, a benzoyl group or an alkanoyl group comprising any of the $C_1$-$C_4$ alkyl groups mentioned above, such as an acetyl or propionyl group.

The non-naturally occurring amino acids are suitably resistant or insensitive to common proteases. Examples of non-naturally occurring amino acids that are resistant or insensitive to proteases include the dextrorotatory (D-) form of any of the above-mentioned naturally occurring L-amino acids, as well as L- and/or D-non-naturally occurring amino acids. The D-amino acids do not normally occur in proteins, although they are found in certain peptide antibiotics that are synthesized by means other than the normal ribosomal protein synthetic machinery of the cell. As used herein, the D-amino acids are considered to be non-naturally occurring amino acids.

In order to minimize protease sensitivity, the peptides should have less than five, preferably less than four, more preferably less than three, and most preferably, less than two contiguous L-amino acids recognized by common proteases, irrespective of whether the amino acids are naturally or non-naturally occurring. Optimally, the peptide has only D-amino acids, and no L-amino acids. If the peptide contains protease sensitive sequences of amino acids, at least one of the amino acids is preferably a non-naturally-occurring D-amino acid, thereby conferring protease resistance. An example of a protease sensitive sequence includes two or more contiguous basic amino acids that are readily cleaved by common proteases, such as endopeptidases and trypsin. Examples of basic amino acids include arginine, lysine and histidine.

The aromatic-cationic peptides should have a minimum number of net positive charges at physiological pH in comparison to the total number of amino acid residues in the peptide. The minimum number of net positive charges at physiological pH will be referred to below as ($p_m$). The total number of amino acid residues in the peptide will be referred to below as (r). The minimum number of net positive charges discussed below are all at physiological pH. The term "physiological pH" as used herein refers to the normal pH in the cells of the tissues and organs of the mammalian body. For instance, the physiological pH of a human is normally approximately 7.4, but normal physiological pH in mammals may be any pH from about 7.0 to about 7.8.

Typically, an aromatic-cationic peptide has a positively charged N-terminal amino group and a negatively charged C-terminal carboxyl group. The charges cancel each other out at physiological pH. As an example of calculating net charge, the peptide Tyr-Arg-Phe-Lys-Glu-His-Trp-D-Arg has one negatively charged amino acid (i.e., Glu) and four positively charged amino acids (i.e., two Arg residues, one Lys, and one His). Therefore, the above peptide has a net positive charge of three.

In one embodiment, the aromatic-cationic peptides have a relationship between the minimum number of net positive charges at physiological pH ($p_m$) and the total number of amino acid residues (r) wherein $3p_m$ is the largest number that is less than or equal to r+1. In this embodiment, the relationship between the minimum number of net positive charges ($p_m$) and the total number of amino acid residues (r) is as follows:

TABLE 1

| Amino acid number and net positive charges ($3p_m \le p + 1$) | | | | | | | | | | | | | | | | | | |
|---|---|---|---|---|---|---|---|---|---|---|---|---|---|---|---|---|---|---|
| (r) | 3 | 4 | 5 | 6 | 7 | 8 | 9 | 10 | 11 | 12 | 13 | 14 | 15 | 16 | 17 | 18 | 19 | 20 |
| ($p_m$) | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of net positive charges ($p_m$) and the total number of amino acid residues (r) wherein $2p_m$ is the largest number that is less than or equal to r+1. In this embodiment, the relationship between the minimum number of net positive charges ($p_m$) and the total number of amino acid residues (r) is as follows:

TABLE 2

| Amino acid number and net positive charges ($2p_m \le p + 1$) | | | | | | | | | | | | | | | | | | |
|---|---|---|---|---|---|---|---|---|---|---|---|---|---|---|---|---|---|---|
| (r) | 3 | 4 | 5 | 6 | 7 | 8 | 9 | 10 | 11 | 12 | 13 | 14 | 15 | 16 | 17 | 18 | 19 | 20 |
| ($p_m$) | 2 | 2 | 3 | 3 | 4 | 4 | 5 | 5 | 6 | 6 | 7 | 7 | 8 | 8 | 9 | 9 | 10 | 10 |

In one embodiment, the minimum number of net positive charges ($p_m$) and the total number of amino acid residues (r) are equal. In another embodiment, the peptides have three or four amino acid residues and a minimum of one net positive charge, suitably, a minimum of two net positive charges and more preferably a minimum of three net positive charges.

It is also important that the aromatic-cationic peptides have a minimum number of aromatic groups in comparison to the total number of net positive charges ($p_t$). The minimum number of aromatic groups will be referred to below as (a). Naturally occurring amino acids that have an aromatic group include the amino acids histidine, tryptophan, tyrosine, and phenylalanine. For example, the hexapeptide Lys-Gln-Tyr-D-Arg-Phe-Trp has a net positive charge of two (contributed by the lysine and arginine residues) and three aromatic groups (contributed by tyrosine, phenylalanine and tryptophan residues).

The aromatic-cationic peptides should also have a relationship between the minimum number of aromatic groups (a) and the total number of net positive charges at physiological pH ($p_t$) wherein 3a is the largest number that is less than or equal to $p_t$+1, except that when $p_t$ is 1, a may also be 1. In this embodiment, the relationship between the minimum number of aromatic groups (a) and the total number of net positive charges ($p_t$) is as follows:

TABLE 3

Aromatic groups and net positive charges (3a ≤ $p_t$ + 1 or a = $p_t$ = 1)

| ($p_t$) | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| (a) | 1 | 1 | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of aromatic groups (a) and the total number of net positive charges ($p_t$) wherein 2a is the largest number that is less than or equal to $p_t$+1. In this embodiment, the relationship between the minimum number of aromatic amino acid residues (a) and the total number of net positive charges ($p_t$) is as follows:

TABLE 4

Aromatic groups and net positive charges (2a ≤ $p_t$ + 1 or a = $p_t$ = 1)

| ($p_t$) | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| (a) | 1 | 1 | 2 | 2 | 3 | 3 | 4 | 4 | 5 | 5 | 6 | 6 | 7 | 7 | 8 | 8 | 9 | 9 | 10 | 10 |

In another embodiment, the number of aromatic groups (a) and the total number of net positive charges ($p_t$) are equal.

Carboxyl groups, especially the terminal carboxyl group of a C-terminal amino acid, are suitably amidated with, for example, ammonia to form the C-terminal amide. Alternatively, the terminal carboxyl group of the C-terminal amino acid may be amidated with any primary or secondary amine. The primary or secondary amine may, for example, be an alkyl, especially a branched or unbranched $C_1$-$C_4$ alkyl, or an aryl amine. Accordingly, the amino acid at the C-terminus of the peptide may be converted to an amido, N-methylamido, N-ethylamido, N,N-dimethylamido, N,N-diethylamido, N-methyl-N-ethylamido, N-phenylamido or N-phenyl-N-ethylamido group. The free carboxylate groups of the asparagine, glutamine, aspartic acid, and glutamic acid residues not occurring at the C-terminus of the aromatic-cationic peptides may also be amidated wherever they occur within the peptide. The amidation at these internal positions may be with ammonia or any of the primary or secondary amines described above.

In one embodiment, the aromatic-cationic peptide is a tripeptide having two net positive charges and at least one aromatic amino acid. In a particular embodiment, the aromatic-cationic peptide is a tripeptide having two net positive charges and two aromatic amino acids.

Aromatic-cationic peptides include, but are not limited to, the following peptide examples:

Lys-D-Arg-Tyr-$NH_2$

Phe-D-Arg-His

D-Tyr-Trp-Lys-$NH_2$

Trp-D-Lys-Tyr-Arg-$NH_2$

Tyr-His-D-Gly-Met

Phe-Arg-D-His-Asp

Tyr-D-Arg-Phe-Lys-Glu-$NH_2$

Met-Tyr-D-Lys-Phe-Arg

D-His-Glu-Lys-Tyr-D-Phe-Arg

Lys-D-Gln-Tyr-Arg-D-Phe-Trp-$NH_2$

Phe-D-Arg-Lys-Trp-Tyr-D-Arg-His

Gly-D-Phe-Lys-Tyr-His-D-Arg-Tyr-$NH_2$

Val-D-Lys-His-Tyr-D-Phe-Ser-Tyr-Arg-$NH_2$

Trp-Lys-Phe-D-Asp-Arg-Tyr-D-His-Lys

Lys-Trp-D-Tyr-Arg-Asn-Phe-Tyr-D-His-$NH_2$

Thr-Gly-Tyr-Arg-D-His-Phe-Trp-D-His-Lys

Asp-D-Trp-Lys-Tyr-D-His-Phe-Arg-D-Gly-Lys-$NH_2$

D-His-Lys-Tyr-D-Phe-Glu-D-Asp-D-His-D-Lys-Arg-Trp-$NH_2$

Ala-D-Phe-D-Arg-Tyr-Lys-D-Trp-His-D-Tyr-Gly-Phe

Tyr-D-His-Phe-D-Arg-Asp-Lys-D-Arg-His-Trp-D-His-Phe

Phe-Phe-D-Tyr-Arg-Glu-Asp-D-Lys-Arg-D-Arg-His-Phe-$NH_2$

Phe-Try-Lys-D-Arg-Trp-His-D-Lys-D-Lys-Glu-Arg-D-Tyr-Thr

Tyr-Asp-D-Lys-Tyr-Phe-D-Lys-D-Arg-Phe-Pro-D-Tyr-His-Lys

Glu-Arg-D-Lys-Tyr-D-Val-Phe-D-His-Trp-Arg-D-Gly-Tyr-Arg-D-Met-$NH_2$

Arg-D-Leu-D-Tyr-Phe-Lys-Glu-D-Lys-Arg-D-Trp-Lys-D-Phe-Tyr-D-Arg-Gly

D-Glu-Asp-Lys-D-Arg-D-His-Phe-Phe-D-Val-Tyr-Arg-Tyr-D-Tyr-Arg-His-Phe-$NH_2$

Asp-Arg-D-Phe-Cys-Phe-D-Arg-D-Lys-Tyr-Arg-D-Tyr-Trp-D-His-Tyr-D-Phe-Lys-Phe

His-Tyr-D-Arg-Trp-Lys-Phe-D-Asp-Ala-Arg-Cys-D-Tyr-His-Phe-D-Lys-Tyr-His-Ser-$NH_2$

Gly-Ala-Lys-Phe-D-Lys-Glu-Arg-Tyr-His-D-Arg-D-Arg-Asp-Tyr-Trp-D-His-Trp-His-D-Lys-Asp

Thr-Tyr-Arg-D-Lys-Trp-Tyr-Glu-Asp-D-Lys-D-Arg-His-Phe-D-Tyr-Gly-Val-Ile-D-His-Arg-Tyr-Lys-$NH_2$

In one embodiment, the peptides have mu-opioid receptor agonist activity (i.e., they activate the mu-opioid receptor).

Peptides, which have mu-opioid receptor agonist activity, are typically those peptides, which have a tyrosine residue or a tyrosine derivative at the N-terminus (i.e., the first amino acid position). Suitable derivatives of tyrosine include 2'-methyltyrosine (Mmt); 2',6'-dimethyltyrosine (2'6'-Dmt); 3',5'-dimethyltyrosine (3'5'Dmt); N,2',6'-trimethyltyrosine (Tmt); and 2'-hydroxy-6'-methyltryosine (Hmt).

In one embodiment, a peptide that has mu-opioid receptor agonist activity has the formula Tyr-D-Arg-Phe-Lys-NH$_2$. Tyr-D-Arg-Phe-Lys-NH$_2$ has a net positive charge of three, contributed by the amino acids tyrosine, arginine, and lysine and has two aromatic groups contributed by the amino acids phenylalanine and tyrosine. The tyrosine of Tyr-D-Arg-Phe-Lys-NH$_2$ can be a modified derivative of tyrosine such as in 2',6'-dimethyltyrosine to produce the compound having the formula 2',6'-Dmt-D-Arg-Phe-Lys-NH$_2$. 2',6'-Dmt-D-Arg-Phe-Lys-NH$_2$ has a molecular weight of 640 and carries a net three positive charge at physiological pH. 2',6'-Dmt-D-Arg-Phe-Lys-NH$_2$ readily penetrates the plasma membrane of several mammalian cell types in an energy-independent manner (Zhao et al., *J. Pharmacol Exp Ther.,* 304:425-432, 2003).

Alternatively, in other instances, the aromatic-cationic peptide does not have mu-opioid receptor agonist activity. For example, during long-term treatment, such as in a chronic disease state or condition, the use of an aromatic-cationic peptide that activates the mu-opioid receptor may be contraindicated. In these instances, the potentially adverse or addictive effects of the aromatic-cationic peptide may preclude the use of an aromatic-cationic peptide that activates the mu-opioid receptor in the treatment regimen of a human patient or other mammal. Potential adverse effects may include sedation, constipation and respiratory depression. In such instances an aromatic-cationic peptide that does not activate the mu-opioid receptor may be an appropriate treatment. Peptides that do not have mu-opioid receptor agonist activity generally do not have a tyrosine residue or a derivative of tyrosine at the N-terminus (i.e., amino acid position 1). The amino acid at the N-terminus can be any naturally occurring or non-naturally occurring amino acid other than tyrosine. In one embodiment, the amino acid at the N-terminus is phenylalanine or its derivative. Exemplary derivatives of phenylalanine include 2'-methylphenylalanine (Mmp), 2',6'-dimethylphenylalanine (2',6'-Dmp), N,2',6'-trimethylphenylalanine (Tmp), and 2'-hydroxy-6'-methylphenylalanine (Hmp).

An example of an aromatic-cationic peptide that does not have mu-opioid receptor agonist activity has the formula Phe-D-Arg-Phe-Lys-NH$_2$. Alternatively, the N-terminal phenylalanine can be a derivative of phenylalanine such as 2',6'-dimethylphenylalanine (2'6'-Dmp). Tyr-D-Arg-Phe-Lys-NH$_2$ containing 2',6'-dimethylphenylalanine at amino acid position 1 has the formula 2',6'-Dmp-D-Arg-Phe-Lys-NH$_2$. In one embodiment, the amino acid sequence of 2',6'-Dmt-D-Arg-Phe-Lys-NH$_2$ is rearranged such that Dmt is not at the N-terminus. An example of such an aromatic-cationic peptide that does not have mu-opioid receptor agonist activity has the formula D-Arg-2'6'-Dmt-Lys-Phe-NH$_2$.

Suitable substitution variants of the peptides listed herein include conservative amino acid substitutions. Amino acids may be grouped according to their physicochemical characteristics as follows:

(a) Non-polar amino acids: Ala(A) Ser(S) Thr(T) Pro(P) Gly(G) Cys (C);
(b) Acidic amino acids: Asn(N) Asp(D) Glu(E) Gln(Q);
(c) Basic amino acids: His(H) Arg(R) Lys(K);
(d) Hydrophobic amino acids: Met(M) Leu(L) Ile(I) Val (V); and
(e) Aromatic amino acids: Phe(F) Tyr(Y) Trp(W) His (H).

Substitutions of an amino acid in a peptide by another amino acid in the same group is referred to as a conservative substitution and may preserve the physicochemical characteristics of the original peptide. In contrast, substitutions of an amino acid in a peptide by another amino acid in a different group is generally more likely to alter the characteristics of the original peptide.

Examples of peptides that activate mu-opioid receptors include, but are not limited to, the aromatic-cationic peptides shown in Table 5.

TABLE 5

Peptide Analogs with Mu-Opioid Activity

| Amino Acid Position 1 | Amino Acid Position 2 | Amino Acid Position 3 | Amino Acid Position 4 | C-Terminal Modification |
|---|---|---|---|---|
| Tyr | D-Arg | Phe | Lys | NH$_2$ |
| Tyr | D-Arg | Phe | Orn | NH$_2$ |
| Tyr | D-Arg | Phe | Dab | NH$_2$ |
| Tyr | D-Arg | Phe | Dap | NH$_2$ |
| 2'6'Dmt | D-Arg | Phe | Lys | NH$_2$ |
| 2'6'Dmt | D-Arg | Phe | Lys-NH(CH$_2$)$_2$—NH-dns | NH$_2$ |
| 2'6'Dmt | D-Arg | Phe | Lys-NH(CH$_2$)$_2$—NH-atn | NH$_2$ |
| 2'6'Dmt | D-Arg | Phe | dnsLys | NH$_2$ |
| 2'6'Dmt | D-Cit | Phe | Lys | NH$_2$ |
| 2'6'Dmt | D-Cit | Phe | Ahp | NH$_2$ |
| 2'6'Dmt | D-Arg | Phe | Orn | NH$_2$ |
| 2'6'Dmt | D-Arg | Phe | Dab | NH$_2$ |
| 2'6'Dmt | D-Arg | Phe | Dap | NH$_2$ |
| 2'6'Dmt | D-Arg | Phe | Ahp(2-aminoheptanoic acid) | NH$_2$ |
| Bio-2'6'Dmt | D-Arg | Phe | Lys | NH$_2$ |
| 3'5'Dmt | D-Arg | Phe | Lys | NH$_2$ |
| 3'5'Dmt | D-Arg | Phe | Orn | NH$_2$ |
| 3'5'Dmt | D-Arg | Phe | Dab | NH$_2$ |
| 3'5'Dmt | D-Arg | Phe | Dap | NH$_2$ |
| Tyr | D-Arg | Tyr | Lys | NH$_2$ |
| Tyr | D-Arg | Tyr | Orn | NH$_2$ |
| Tyr | D-Arg | Tyr | Dab | NH$_2$ |
| Tyr | D-Arg | Tyr | Dap | NH$_2$ |
| 2'6'Dmt | D-Arg | Tyr | Lys | NH$_2$ |
| 2'6'Dmt | D-Arg | Tyr | Orn | NH$_2$ |
| 2'6'Dmt | D-Arg | Tyr | Dab | NH$_2$ |

TABLE 5-continued

Peptide Analogs with Mu-Opioid Activity

| Amino Acid Position 1 | Amino Acid Position 2 | Amino Acid Position 3 | Amino Acid Position 4 | C-Terminal Modification |
|---|---|---|---|---|
| 2'6'Dmt | D-Arg | Tyr | Dap | $NH_2$ |
| 2'6'Dmt | D-Arg | 2'6'Dmt | Lys | $NH_2$ |
| 2'6'Dmt | D-Arg | 2'6'Dmt | Orn | $NH_2$ |
| 2'6'Dmt | D-Arg | 2'6'Dmt | Dab | $NH_2$ |
| 2'6'Dmt | D-Arg | 2'6'Dmt | Dap | $NH_2$ |
| 3'5'Dmt | D-Arg | 3'5'Dmt | Arg | $NH_2$ |
| 3'5'Dmt | D-Arg | 3'5'Dmt | Lys | $NH_2$ |
| 3'5'Dmt | D-Arg | 3'5'Dmt | Orn | $NH_2$ |
| 3'5'Dmt | D-Arg | 3'5'Dmt | Dab | $NH_2$ |
| Tyr | D-Lys | Phe | Dap | $NH_2$ |
| Tyr | D-Lys | Phe | Arg | $NH_2$ |
| Tyr | D-Lys | Phe | Lys | $NH_2$ |
| Tyr | D-Lys | Phe | Orn | $NH_2$ |
| 2'6'Dmt | D-Lys | Phe | Dab | $NH_2$ |
| 2'6'Dmt | D-Lys | Phe | Dap | $NH_2$ |
| 2'6'Dmt | D-Lys | Phe | Arg | $NH_2$ |
| 2'6'Dmt | D-Lys | Phe | Lys | $NH_2$ |
| 3'5'Dmt | D-Lys | Phe | Orn | $NH_2$ |
| 3'5'Dmt | D-Lys | Phe | Dab | $NH_2$ |
| 3'5'Dmt | D-Lys | Phe | Dap | $NH_2$ |
| 3'5'Dmt | D-Lys | Phe | Arg | $NH_2$ |
| Tyr | D-Lys | Tyr | Lys | $NH_2$ |
| Tyr | D-Lys | Tyr | Orn | $NH_2$ |
| Tyr | D-Lys | Tyr | Dab | $NH_2$ |
| Tyr | D-Lys | Tyr | Dap | $NH_2$ |
| 2'6'Dmt | D-Lys | Tyr | Lys | $NH_2$ |
| 2'6'Dmt | D-Lys | Tyr | Orn | $NH_2$ |
| 2'6'Dmt | D-Lys | Tyr | Dab | $NH_2$ |
| 2'6'Dmt | D-Lys | Tyr | Dap | $NH_2$ |
| 2'6'Dmt | D-Lys | 2'6'Dmt | Lys | $NH_2$ |
| 2'6'Dmt | D-Lys | 2'6'Dmt | Orn | $NH_2$ |
| 2'6'Dmt | D-Lys | 2'6'Dmt | Dab | $NH_2$ |
| 2'6'Dmt | D-Lys | 2'6'Dmt | Dap | $NH_2$ |
| 2'6'Dmt | D-Arg | Phe | dnsDap | $NH_2$ |
| 2'6'Dmt | D-Arg | Phe | atnDap | $NH_2$ |
| 3'5'Dmt | D-Lys | 3'5'Dmt | Lys | $NH_2$ |
| 3'5'Dmt | D-Lys | 3'5'Dmt | Orn | $NH_2$ |
| 3'5'Dmt | D-Lys | 3'5'Dmt | Dab | $NH_2$ |
| 3'5'Dmt | D-Lys | 3'5'Dmt | Dap | $NH_2$ |
| Tyr | D-Lys | Phe | Arg | $NH_2$ |
| Tyr | D-Orn | Phe | Arg | $NH_2$ |
| Tyr | D-Dab | Phe | Arg | $NH_2$ |
| Tyr | D-Dap | Phe | Arg | $NH_2$ |
| 2'6'Dmt | D-Arg | Phe | Arg | $NH_2$ |
| 2'6'Dmt | D-Lys | Phe | Arg | $NH_2$ |
| 2'6'Dmt | D-Orn | Phe | Arg | $NH_2$ |
| 2'6'Dmt | D-Dab | Phe | Arg | $NH_2$ |
| 3'5'Dmt | D-Dap | Phe | Arg | $NH_2$ |
| 3'5'Dmt | D-Arg | Phe | Arg | $NH_2$ |
| 3'5'Dmt | D-Lys | Phe | Arg | $NH_2$ |
| 3'5'Dmt | D-Orn | Phe | Arg | $NH_2$ |
| Tyr | D-Lys | Tyr | Arg | $NH_2$ |
| Tyr | D-Orn | Tyr | Arg | $NH_2$ |
| Tyr | D-Dab | Tyr | Arg | $NH_2$ |
| Tyr | D-Dap | Tyr | Arg | $NH_2$ |
| 2'6'Dmt | D-Arg | 2'6'Dmt | Arg | $NH_2$ |
| 2'6'Dmt | D-Lys | 2'6'Dmt | Arg | $NH_2$ |
| 2'6'Dmt | D-Orn | 2'6'Dmt | Arg | $NH_2$ |
| 2'6'Dmt | D-Dab | 2'6'Dmt | Arg | $NH_2$ |
| 3'5'Dmt | D-Dap | 3'5'Dmt | Arg | $NH_2$ |
| 3'5'Dmt | D-Arg | 3'5'Dmt | Arg | $NH_2$ |
| 3'5'Dmt | D-Lys | 3'5'Dmt | Arg | $NH_2$ |
| 3'5'Dmt | D-Orn | 3'5'Dmt | Arg | $NH_2$ |
| Mmt | D-Arg | Phe | Lys | $NH_2$ |
| Mmt | D-Arg | Phe | Orn | $NH_2$ |
| Mmt | D-Arg | Phe | Dab | $NH_2$ |
| Mmt | D-Arg | Phe | Dap | $NH_2$ |
| Tmt | D-Arg | Phe | Lys | $NH_2$ |
| Tmt | D-Arg | Phe | Orn | $NH_2$ |
| Tmt | D-Arg | Phe | Dab | $NH_2$ |
| Tmt | D-Arg | Phe | Dap | $NH_2$ |
| Hmt | D-Arg | Phe | Lys | $NH_2$ |
| Hmt | D-Arg | Phe | Orn | $NH_2$ |
| Hmt | D-Arg | Phe | Dab | $NH_2$ |
| Hmt | D-Arg | Phe | Dap | $NH_2$ |

TABLE 5-continued

Peptide Analogs with Mu-Opioid Activity

| Amino Acid Position 1 | Amino Acid Position 2 | Amino Acid Position 3 | Amino Acid Position 4 | C-Terminal Modification |
|---|---|---|---|---|
| Mmt | D-Lys | Phe | Lys | $NH_2$ |
| Mmt | D-Lys | Phe | Orn | $NH_2$ |
| Mmt | D-Lys | Phe | Dab | $NH_2$ |
| Mmt | D-Lys | Phe | Dap | $NH_2$ |
| Mmt | D-Lys | Phe | Arg | $NH_2$ |
| Tmt | D-Lys | Phe | Lys | $NH_2$ |
| Tmt | D-Lys | Phe | Orn | $NH_2$ |
| Tmt | D-Lys | Phe | Dab | $NH_2$ |
| Tmt | D-Lys | Phe | Dap | $NH_2$ |
| Tmt | D-Lys | Phe | Arg | $NH_2$ |
| Hmt | D-Lys | Phe | Lys | $NH_2$ |
| Hmt | D-Lys | Phe | Orn | $NH_2$ |
| Hmt | D-Lys | Phe | Dab | $NH_2$ |
| Hmt | D-Lys | Phe | Dap | $NH_2$ |
| Hmt | D-Lys | Phe | Arg | $NH_2$ |
| Mmt | D-Lys | Phe | Arg | $NH_2$ |
| Mmt | D-Orn | Phe | Arg | $NH_2$ |
| Mmt | D-Dab | Phe | Arg | $NH_2$ |
| Mmt | D-Dap | Phe | Arg | $NH_2$ |
| Mmt | D-Arg | Phe | Arg | $NH_2$ |
| Tmt | D-Lys | Phe | Arg | $NH_2$ |
| Tmt | D-Orn | Phe | Arg | $NH_2$ |
| Tmt | D-Dab | Phe | Arg | $NH_2$ |
| Tmt | D-Dap | Phe | Arg | $NH_2$ |
| Tmt | D-Arg | Phe | Arg | $NH_2$ |
| Hmt | D-Lys | Phe | Arg | $NH_2$ |
| Hmt | D-Orn | Phe | Arg | $NH_2$ |
| Hmt | D-Dab | Phe | Arg | $NH_2$ |
| Hmt | D-Dap | Phe | Arg | $NH_2$ |
| Hmt | D-Arg | Phe | Arg | $NH_2$ |

Dab = diaminobutyric
Dap = diaminopropionic acid
Dmt = dimethyltyrosine
Mmt = 2'-methyltyrosine
Tmt = N,2',6'-trimethyltyrosine
Hmt = 2'-hydroxy,6'-methyltyrosine
dnsDap = β-dansyl-L-α,β-diaminopropionic acid
atnDap = β-anthraniloyl-L-α,β-diaminopropionic acid
Bio = biotin Examples of peptides that do not activate mu-opioid receptors include, but are not limited to, the aromatic-cationic peptides shown in Table 6.

TABLE 6

Peptide Analogs Lacking Mu-Opioid Activity

| Amino Acid Position 1 | Amino Acid Position 2 | Amino Acid Position 3 | Amino Acid Position 4 | C-Terminal Modification |
|---|---|---|---|---|
| D-Arg | Dmt | Lys | Phe | $NH_2$ |
| D-Arg | Dmt | Phe | Lys | $NH_2$ |
| D-Arg | Phe | Lys | Dmt | $NH_2$ |
| D-Arg | Phe | Dmt | Lys | $NH_2$ |
| D-Arg | Lys | Dmt | Phe | $NH_2$ |
| D-Arg | Lys | Phe | Dmt | $NH_2$ |
| Phe | Lys | Dmt | D-Arg | $NH_2$ |
| Phe | Lys | D-Arg | Dmt | $NH_2$ |
| Phe | D-Arg | Phe | Lys | $NH_2$ |
| Phe | D-Arg | Dmt | Lys | $NH_2$ |
| Phe | D-Arg | Lys | Dmt | $NH_2$ |
| Phe | Dmt | D-Arg | Lys | $NH_2$ |
| Phe | Dmt | Lys | D-Arg | $NH_2$ |
| Lys | Phe | D-Arg | Dmt | $NH_2$ |
| Lys | Phe | Dmt | D-Arg | $NH_2$ |
| Lys | Dmt | D-Arg | Phe | $NH_2$ |
| Lys | Dmt | Phe | D-Arg | $NH_2$ |
| Lys | D-Arg | Phe | Dmt | $NH_2$ |
| Lys | D-Arg | Dmt | Phe | $NH_2$ |
| D-Arg | Dmt | D-Arg | Phe | $NH_2$ |
| D-Arg | Dmt | D-Arg | Dmt | $NH_2$ |
| D-Arg | Dmt | D-Arg | Tyr | $NH_2$ |
| D-Arg | Dmt | D-Arg | Trp | $NH_2$ |
| Trp | D-Arg | Phe | Lys | $NH_2$ |
| Trp | D-Arg | Tyr | Lys | $NH_2$ |
| Trp | D-Arg | Trp | Lys | $NH_2$ |
| Trp | D-Arg | Dmt | Lys | $NH_2$ |
| D-Arg | Trp | Lys | Phe | $NH_2$ |
| D-Arg | Trp | Phe | Lys | $NH_2$ |
| D-Arg | Trp | Lys | Dmt | $NH_2$ |
| D-Arg | Trp | Dmt | Lys | $NH_2$ |
| D-Arg | Lys | Trp | Phe | $NH_2$ |
| D-Arg | Lys | Trp | Dmt | $NH_2$ |
| Cha | D-Arg | Phe | Lys | $NH_2$ |
| Ala | D-Arg | Phe | Lys | $NH_2$ |

Cha = cyclohexyl alanine

The amino acids of the peptides shown in the tables above may be in either the L- or the D-configuration.

The peptides may be synthesized by any of the methods well known in the art. Suitable methods for chemically synthesizing the protein include, for example, those described by Stuart and Young in *Solid Phase Peptide*

*Synthesis*, Second Edition, Pierce Chemical Company (1984), and in *Methods Enzymol.*, 289, Academic Press, Inc., New York (1997).

Left Ventricular Remodeling

Following myocardial infarction there is a dynamic and progressive LV remodeling that contributes to LV dilation, heart failure, and death. Within the first week of a myocardial infarction (MI) the necrotic zone thins and stretches (infarct expansion) contributing to regional dilation of the infarct zone. This phenomenon increases LV wall stress, thus, increasing oxygen demand. To help compensate for the loss of myocardium and reduced stroke volume, the LV develops global dilation and the non-infarcted wall of the LV develops eccentric hypertrophy whereby sarcomeres are added on in a circumferential or lengthwise fashion. As the ventricle dilates this process initially helps to compensate for reduced stroke volume, but eventually progressive dilatation and hypertrophy lead to congestive heart failure. One of the strongest predictors of death one year post MI is the volume of the left ventricle. The more dilated the left ventricle, the greater the chance of death. Structural and functional abnormalities of the non-infarcted myocardium and myocardium in the infarct border zone may contribute to the LV remodeling phenomenon. Abnormalities in myocardium cell structure can lead to reduced function of the muscles needed to support the weakened heart. In some embodiments, the aromatic-cationic peptide is administered to the subject, chronically, post myocardial infarction.

The compositions and methods disclosed herein are not intended to be limited by the cause of myocardial infarction and/or LV remodeling. By way of example, but not by way of limitation, myocardial infarction may result from hypertension; ischemic heart disease; exposure to a cardiotoxic compound; myocarditis; thyroid disease; viral infection; gingivitis; drug abuse; alcohol abuse; pericarditis; atherosclerosis; vascular disease; hypertrophic cardiomyopathy; acute myocardial infarction; left ventricular systolic dysfunction; heart failure; coronary bypass surgery; starvation; an eating disorder; or a genetic defect.

Stabilization of SERCA2a

As discussed above, the non-infarct myocardium around the infarct, i.e., border zone cells, change their structure to compensate for reduced stroke volume. Sarco/endoplasmic reticulum $Ca^{2+}$-ATPase (SERCA) is a calcium ATPase-type P-ATPase. SERCA is located in the sarcoplasmic reticulum (SR) within muscle cells. $Ca^{2+}$ ATPases transfer $Ca^{2+}$ from the cytosol of the cell to the lumen of the SR at the expense of ATP hydrolysis during muscle relaxation. There are three major paralogs of SERCA: SERCA1, SERCA2, and SERCA3.

During heart failure, the $Ca^{2+}$ transport in ventricular myocytes is altered, which causes an impaired efflux of cytosolic $Ca^{2+}$. Decreased expression and activity of SERCA2a is recognized as a hallmark of heart failure (Schwartz, R. and Yeh, T. "Weighing in on Heart Failure: The Role of SERCA2a SUMOylation." *Nature*. 477: 601-605 (2011)). Additionally, decreased expression of SERCA2a is seen after myocardial infarction (Zarain-Herzberg et al. "Decreased expression of cardiac sarcoplasmic reticulum Ca2+-pump ATPase in congestive heart failure due to myocardial infarction." *Dev. Mol. and Cell. Bio.* 19: 285-290 (1996)). Current studies are directed at raising SERCA2a expression to protect against heart failure and left ventricular remodeling (Niwano et al. "Lentiviral Vector-mediated SERCA2 Gene Transfer Protects Against Heart Failure and Left Ventricular Remodeling After Myocardial Infarction in Rats." *Molecular Therapy.* 16(6): 1026-1032 (2008)). Restoration of SERCA 2a in the border zone cells of an infarct will improve the function of the heart at that border zone (regional improvement in function). Additionally, restoration of SERCA2a in the border zone cells will prevent the stretching and thinning of the myocardial infarction (e.g., provide for improved regions function), and will also prevent or reduce left ventricular remodeling and improve global left ventricular function.

In some embodiments, treatment with an aromatic-cationic peptide, such as, e.g., D-Arg-2'6'-Dmt-Lys-Phe-$NH_2$, increases SERCA2a expression in a subject in need thereof. In some embodiments, the increase of SERCA2a expression results in a decrease in LV remodeling and improves LV function.

Improvement in Cardiac Function

In some embodiments, the stabilization (increase) of SERCA2a expression through treatment with an aromatic-cationic peptide, such as, e.g., D-Arg-2'6'-Dmt-Lys-Phe-$NH_2$, improves the cardiac function of the left ventricle after myocardial infarction. Improvement of LV function includes, but is not limited to, reduced LV volume, improved LV fractional shortening, improved LV ejection fraction, reduced infarct expansion, improved hemodynamics, and reduced lung volumes. In some embodiments, administration of an aromatic-cationic peptide, such as, e.g., D-Arg-2'6'-Dmt-Lys-Phe-$NH_2$, results in an increase in SERCA2a expression, and results in a reduced risk of death and/or heart failure in a subject at risk.

In some embodiments, stabilization of SERCA2a expression through treatment with an aromatic-catoinic peptide, such as D-Arg-2'6'-Dmt-Lys-Phe-$NH_2$, reduces scarring in the left ventricle post infarction. Reduction in scarring includes, but is not limited to, reduced scar circumference, reduced scar thickness, reduced septum thickness, and a reduced expansion index (which is expressed as: LV cavity area/total LV area×septum thickness/scar thickness).

Prophylactic and Therapeutic Uses of Aromatic-Cationic Peptides.

General. The aromatic-cationic peptides described herein are useful to prevent or treat disease. Specifically, the disclosure provides for both prophylactic and therapeutic methods of treating a subject having or at risk of (susceptible to) LV remodeling by administering an aromatic-cationic peptide such as an aromatic-cationic peptide, such as D-Arg-2'6'-Dmt-Lys-Phe-$NH_2$ or a pharmaceutically acceptable salt thereof, such as acetate or trifluoroacetate salt. Typically, LV remodeling causes an increase in LV end diastolic volume and LV end systolic volume. Usually, stroke volume may initially be preserved but eventually, once heart failure occurs, it is actually reduced (i.e., less blood flows out of the ventricle with each beat). Accordingly, the present methods provide for the prevention and/or treatment of LV remodeling in a subject by administering an effective amount of an aromatic-cationic peptide to a subject in need thereof.

Therapeutic Methods.

In therapeutic applications, compositions or medicaments are administered including an aromatic-cationic peptide such as D-Arg-2'6'-Dmt-Lys-Phe-$NH_2$ or a pharmaceutically acceptable salt thereof, such as acetate or trifluoroacetate salt, to a subject suspected of, or already suffering from such a disease in an amount sufficient to cure, or at least partially arrest, the symptoms of the disease, including its complications and intermediate pathological phenotypes in development of the disease. One aspect of the technology includes methods of stabilizing (e.g., increase) SERCA2a expression (e.g., RNA and/or protein) in a subject for therapeutic purposes. In some embodiments, the therapeutic purpose is to treat LV remodeling. As such, the present technology provides methods of treating an individual afflicted with LV remodeling.

Subjects suffering from LV remodeling can be identified by any or a combination of diagnostic or prognostic assays known in the art. For example, typical symptoms of LV remodeling include reduced LV stroke volume, reduced LV ejection fraction, poor fractional shortening, increased infarct expansion, increased LV end diastolic and systolic volume, poor hemodynamics, increased scar formation in LV myocardium, and increased lung volumes. Symptoms of LV remodeling also include symptoms associated with heart failure such as, e.g., shortness of breath, fatigue, and swelling of the extremities. In some embodiments, a "therapeutically effective amount" of the aromatic-cationic peptide thereof, includes levels in which the physiological effects of decreased expression of SERCA2a, at a minimum, ameliorated. Additionally, or alternatively, in some embodiments, a therapeutically effective amount of the aromatic-cationic peptides includes levels in which the physiological effects of LV remodeling are, at a minimum, ameliorated.

Prophylactic Methods.

In one aspect, the technology provides a method for preventing, in a subject, decreased SERCA2a expression (e.g., RNA and/or protein) by administering to the subject an effective amount of aromatic-cationic peptide, e.g., D-Arg-2'6'-Dmt-Lys-Phe-NH$_2$, or a pharmaceutically acceptable salt thereof such as acetate or trifluoroacetate salt, that prevents decreased SERCA2a expression during or after myocardial infarction. Additionally, or alternatively, in some embodiments, administration of the aromatic-cationic peptide prevents or reduces LV remodeling. In prophylactic applications, pharmaceutical compositions or medicaments of aromatic-cationic peptides are administered to a subject susceptible to, or otherwise at risk of a disease or condition in an amount sufficient to eliminate or reduce the risk, lessen the severity, or delay the outset of the disease, including biochemical, histologic and/or behavioral symptoms of the disease, its complications and intermediate pathological phenotypes presenting during development of the disease. Administration of a prophylactic aromatic-cationic can occur prior to the manifestation of symptoms characteristic of the aberrancy, such that a disease or disorder is prevented or, alternatively, delayed in its progression.

Determination of the Biological Effect of the Aromatic-Cationic Peptide-Based Therapeutic.

In various embodiments, suitable in vitro or in vivo assays are performed to determine the effect of a specific aromatic-cationic peptide-based therapeutic and whether its administration is indicated for treatment. In various embodiments, in vitro assays can be performed with representative animal models, to determine if a given aromatic-cationic peptide-based therapeutic exerts the desired effect in preventing or treating heart failure. Compounds for use in therapy can be tested in suitable animal model systems including, but not limited to rats, mice, chicken, cows, monkeys, rabbits, and the like, prior to testing in human subjects. Similarly, for in vivo testing, any of the animal model system known in the art can be used prior to administration to human subjects.

Modes of Administration and Effective Dosages

Any method known to those in the art for contacting a cell, organ or tissue with a peptide may be employed. Suitable methods include in vitro, ex vivo, or in vivo methods. In vivo methods typically include the administration of an aromatic-cationic peptide, such as those described above, to a mammal, suitably a human. When used in vivo for therapy, the aromatic-cationic peptides are administered to the subject in effective amounts (i.e., amounts that have desired therapeutic effect). The dose and dosage regimen will depend upon the degree of the infection in the subject, the characteristics of the particular aromatic-cationic peptide used, e.g., its therapeutic index, the subject, and the subject's history.

The effective amount may be determined during pre-clinical trials and clinical trials by methods familiar to physicians and clinicians. An effective amount of a peptide useful in the methods may be administered to a mammal in need thereof by any of a number of well-known methods for administering pharmaceutical compounds. The peptide may be administered systemically or locally.

In some embodiments, the aromatic-cationic peptide may be formulated as a pharmaceutically acceptable salt. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (e.g., citric, gluconic, glycolic, lactic, lactobionic, malic, and tartaric acids), aliphatic monocarboxylic acids (e.g., acetic, butyric, formic, propionic and trifluoroacetic acids), amino acids (e.g., aspartic and glutamic acids), aromatic carboxylic acids (e.g., benzoic, p-chlorobenzoic, diphenylacetic, gentisic, hippuric, and triphenylacetic acids), aromatic hydroxyl acids (e.g., o-hydroxybenzoic, p-hydroxybenzoic, 1-hydroxynaphthalene-2-carboxylic and 3-hydroxynaphthalene-2-carboxylic acids), ascorbic, dicarboxylic acids (e.g., fumaric, maleic, oxalic and succinic acids), glucuronic, mandelic, mucic, nicotinic, orotic, pamoic, pantothenic, sulfonic acids (e.g., benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like. In some embodiments, the salt is an acetate or trifluoroacetate salt.

The aromatic-cationic peptides described herein can be incorporated into pharmaceutical compositions for administration, singly or in combination, to a subject for the treatment or prevention of a disorder described herein. Such compositions typically include the active agent and a pharmaceutically acceptable carrier. Supplementary active compounds can also be incorporated into the compositions.

Pharmaceutical compositions are typically formulated to be compatible with its intended route of administration. Examples of routes of administration include parenteral (e.g., intravenous, intradermal, intraperitoneal or subcutaneous), oral, inhalation, transdermal (topical), intraocular, iontophoretic, and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. For convenience of the patient or treating physician, the dosing formulation can be provided in a kit containing all necessary equipment (e.g., vials of drug, vials of diluent, syringes and needles) for a treatment course (e.g., 7 days of treatment).

Pharmaceutical compositions suitable for injectable use can include sterile aqueous solutions (where water-soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, a composition for parenteral administration must be sterile and should be fluid to the extent that easy syringability exists. It should be stable under the conditions of manufacture and storage and must be preserved against the contaminating action of microorganisms such as bacteria and fungi.

The aromatic-cationic peptide compositions can include a carrier, which can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thiomerasol, and the like. Glutathione and other antioxidants can be included to prevent oxidation. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, aluminum monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressurized container or dispenser, which contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays. For transdermal administration, the active compounds are formulated into ointments, salves, gels, or creams as generally known in the art. In one embodiment, transdermal administration may be performed my iontophoresis.

A therapeutic aromatic-cationic protein or aromatic-cationic peptide can be formulated in a carrier system. The carrier can be a colloidal system. The colloidal system can be a liposome, a phospholipid bilayer vehicle. In one embodiment, the therapeutic peptide is encapsulated in a liposome while maintaining peptide integrity. As one skilled in the art would appreciate, there are a variety of methods to prepare liposomes. See Lichtenberg et al., *Methods Biochem. Anal.*, 33:337-462 (1988); Anselem et al., *Liposome Technology*, CRC Press (1993). Liposomal formulations can delay clearance and increase cellular uptake. See Reddy, *Ann. Pharmacother.*, 34(7-8):915-923 (2000). An active agent can also be loaded into a particle prepared from pharmaceutically acceptable ingredients including, but not limited to, soluble, insoluble, permeable, impermeable, biodegradable or gastroretentive polymers or liposomes. Such particles include, but are not limited to, e.g., nanoparticles, biodegradable nanoparticles, microparticles, biodegradable microparticles, nanospheres, biodegradable nanospheres, microspheres, biodegradable microspheres, capsules, emulsions, liposomes, micelles, and viral vector systems.

The carrier can also be a polymer, e.g., a biodegradable, biocompatible polymer matrix. In one embodiment, the therapeutic peptide can be embedded in the polymer matrix, while maintaining protein integrity. The polymer may be natural, such as polypeptides, proteins or polysaccharides, or synthetic, such as poly α-hydroxy acids. Examples include carriers made of, e.g., collagen, fibronectin, elastin, cellulose acetate, cellulose nitrate, polysaccharide, fibrin, gelatin, and combinations thereof. In one embodiment, the polymer is poly-lactic acid (PLA) or copoly lactic/glycolic acid (PGLA). The polymeric matrices can be prepared and isolated in a variety of forms and sizes, including microspheres and nanospheres. Polymer formulations can lead to prolonged duration of therapeutic effect. (See Reddy, *Ann. Pharmacother.*, 34(7-8):915-923 (2000)). A polymer formulation for human growth hormone (hGH) has been used in clinical trials. See Kozarich and Rich, *Chemical Biology*, 2:548-552 (1998).

Examples of polymer microsphere sustained release formulations are described in PCT publication WO 99/15154 (Tracy et al.), U.S. Pat. Nos. 5,674,534 and 5,716,644 (both to Zale et al.), PCT publication WO 96/40073 (Zale et al.), and PCT publication WO 00/38651 (Shah et al.). U.S. Pat. Nos. 5,674,534 and 5,716,644 and PCT publication WO 96/40073 describe a polymeric matrix containing particles of erythropoietin that are stabilized against aggregation with a salt.

In some embodiments, therapeutic aromatic-cationic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using known techniques. The carrier materials can be obtained commercially, e.g., from Alza Corporation and Nova Pharmaceuticals, Inc. Liposomal suspensions (including liposomes targeted to specific cells with monoclonal antibodies to cell-specific antigens) can also be used as pharmaceutically acceptable carriers. These can be prepared according to methods known to those skilled in the art, for example, as described in U.S. Pat. No. 4,522,811.

The therapeutic compounds can also be formulated to enhance intracellular delivery. For example, liposomal delivery systems are known in the art, see, e.g., Chonn and Cullis, "Recent Advances in Liposome Drug Delivery Systems," Current Opinion in Biotechnology 6:698-708 (1995); Weiner, "Liposomes for Protein Delivery: Selecting Manufacture and Development Processes," *Immunomethods*, 4(3): 201-9 (1994); and Gregoriadis, "Engineering Liposomes for Drug Delivery: Progress and Problems," *Trends Biotechnol.*, 13(12):527-37 (1995). Mizguchi et al., *Cancer Lett.*, 100: 63-69 (1996), describes the use of fusogenic liposomes to deliver a protein to cells both in vivo and in vitro.

Dosage, toxicity and therapeutic efficacy of the therapeutic agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds, which exhibit high therapeutic indices, are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the 1050 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Typically, an effective amount of the aromatic-cationic peptides, sufficient for achieving a therapeutic or prophylactic effect, range from about 0.000001 mg per kilogram body weight per day to about 10,000 mg per kilogram body weight per day. Suitably, the dosage ranges are from about 0.0001 mg per kilogram body weight per day to about 100 mg per kilogram body weight per day. For example dosages can be 1 mg/kg body weight or 10 mg/kg body weight every day, every two days or every three days or within the range of 1-10 mg/kg every week, every two weeks or every three weeks. In one embodiment, a single dosage of peptide ranges from 0.001-10,000 micrograms per kg body weight. In one embodiment, aromatic-cationic peptide concentrations in a carrier range from 0.2 to 2000 micrograms per delivered milliliter. An exemplary treatment regime entails administration once per day or once a week. In therapeutic applications, a relatively high dosage at relatively short intervals is sometimes required until progression of the disease is reduced or terminated, and preferably until the subject shows partial or complete amelioration of symptoms of disease. Thereafter, the patient can be administered a prophylactic regime.

In some embodiments, a therapeutically effective amount of an aromatic-cationic peptide may be defined as a concentration of peptide at the target tissue of $10^{-12}$ to $10^{-6}$ molar, e.g., approximately $10^{-7}$ molar. This concentration may be delivered by systemic doses of 0.001 to 100 mg/kg or equivalent dose by body surface area. The schedule of doses would be optimized to maintain the therapeutic concentration at the target tissue, most preferably by single daily or weekly administration, but also including continuous administration (e.g., parenteral infusion or transdermal application).

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

The mammal treated in accordance present methods can be any mammal, including, for example, farm animals, such as sheep, pigs, cows, and horses; pet animals, such as dogs and cats; laboratory animals, such as rats, mice and rabbits. In a preferred embodiment, the mammal is a human.

Combination Therapy with an Aromatic-Cationic Peptide and Other Therapeutic Agents In some embodiments, the aromatic-cationic peptides such as D-Arg-2'6'-Dmt-Lys-Phe-NH$_2$ or a pharmaceutically acceptable salt thereof, such as acetate or trifluoroacetate salt, may be combined with one or more additional agents for the prevention or treatment of heart failure and myocardial infarction. Drug treatment for heart failure typically involves diuretics, ACE inhibitors, digoxin (also called digitalis), calcium channel blockers, and beta-blockers. In mild cases, thiazide diuretics, such as hydrochlorothiazide at 25-50 mg/day or chlorothiazide at 250-500 mg/day, are useful. However, supplemental potassium chloride may be needed, since chronic diuresis causes hypokalemis alkalosis. Moreover, thiazide diuretics usually are not effective in patients with advanced symptoms of heart failure. Typical doses of ACE inhibitors include captopril at 25-50 mg/day and quinapril at 10 mg/day.

In some embodiments, an aromatic-cationic peptide such as D-Arg-2'6'-Dmt-Lys-Phe-NH2 or a pharmaceutically acceptable salt thereof, such as acetate or trifluoroacetate salt is combined with an adrenergic beta-2 agonist. An "adrenergic beta-2 agonist" refers to adrenergic beta-2 agonists and analogues and derivatives thereof, including, for example, natural or synthetic functional variants, which have adrenergic beta-2 agonist biological activity, as well as fragments of an adrenergic beta-2 agonist having adrenergic beta-2 agonist biological activity. The term "adrenergic beta-2 agonist biological activity" refers to activity that mimics the effects of adrenaline and noradrenaline in a subject and which improves myocardial contractility in a patient having heart failure. Commonly known adrenergic beta-2 agonists include, but are not limited to, clenbuterol, albuterol, formeoterol, levalbuterol, metaproterenol, pirbuterol, salmeterol, and terbutaline.

In some embodiments, an aromatic-cationic peptide such as D-Arg-2'6'-Dmt-Lys-Phe-NH$_2$ or a pharmaceutically acceptable salt thereof, such as acetate or trifluoroacetate salt, is combined with an adrenergic beta-1 antagonist. Adrenergic beta-1 antagonists and adrenergic beta-1 blockers refer to adrenergic beta-1 antagonists and analogues and derivatives thereof, including, for example, natural or synthetic functional variants which have adrenergic beta-1 antagonist biological activity, as well as fragments of an adrenergic beta-1 antagonist having adrenergic beta-1 antagonist biological activity. Adrenergic beta-1 antagonist biological activity refers to activity that blocks the effects of adrenaline on beta-receptors. Commonly known adrenergic beta-1 antagonists include, but are not limited to, acebutolol, atenolol, betaxolol, bisoprolol, esmolol, and metoprolol.

Clenbuterol, for example, is available under numerous brand names including Spiropent® (Boehinger Ingelheim), Broncodil® (Von Boch I), Broncoterol® (Quimedical PT), Cesbron® (Fidelis PT), and Clenbuter® (Biomedica Foscama). Similarly, methods of preparing adrenergic beta-1 antagonists such as metoprolol and their analogues and derivatives are well-known in the art. Metoprolol, in particular, is commercially available under the brand names Lopressor® (metoprolol tartate) manufactured by Novartis Pharmaceuticals Corporation, One Health Plaza, East Hanover, N.J. 07936-1080. Generic versions of Lopressor® are also available from Mylan Laboratories Inc., 1500 Corporate Drive, Suite 400, Canonsburg, Pa. 15317; and Watson Pharmaceuticals, Inc., 360 Mt. Kemble Ave. Morristown, N.J. 07962. Metoprolol is also commercially available under the brand name Toprol XL®, manufactured by Astra Zeneca, LP.

In some embodiments, an additional therapeutic agent is administered to a subject in combination with an aromatic cationic peptide, such that a synergistic therapeutic effect is produced. Therefore, lower doses of one or both of the therapeutic agents may be used in treating LV remodeling, resulting in increased therapeutic efficacy and decreased side-effects.

In any case, the multiple therapeutic agents may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents.

EXAMPLES

Example 1

D-Arg-2'6'-Dmt-Lys-Phe-NH$_2$ Administered Post-Myocardial Infarction Increases SERCA2a Expression The purpose of this study was to explore the effects of D-Arg-2'6'-Dmt-Lys-Phe-NH$_2$ on SERCA2a expression post-myocardial infarction.
Methods Rats were anesthetized, ventilated, and a thoracotomy performed in the left 4$^{th}$ intercostal space. Temperature was maintained at 36° C. by placing the rats on a heating pad during the procedure. The pericardium was excised and the proximal left coronary artery isolated and permanently occluded with a suture. Coronary artery occlusion was confirmed by cyanosis and akinesis of the anterior wall of the ventricle. The chest was closed, air evacuated, and the rats allowed to recover. Analgesia was administered per the veterinarian. An echocardiogram was obtained at approximately 15 minutes post coronary artery occlusion. At 2 hours rats were randomized to receive chronic daily D-Arg-2'6'-Dmt-Lys-Phe-NH$_2$ (delivered subcutaneously by an Alzet Osmotic Pump—3 mg/kg/day, n=7), water (n=7), sham operation (normal non-infarct hearts, n=7). The Osmotic Pump delivered approximately 0.15 µl/hr for 6 weeks (model 2006; 200 µl). The Alzat pump was implanted subcutaneously between the shoulder blades while the rat was still anesthetized.

After 6 weeks, heart samples were collected from shams, border zone cells of water-treated infarcted hearts (MI/BZ) and D-Arg-2'6'-Dmt-Lys-Phe-NH$_2$-treated hearts (MI/BZ+ AP), and remote noninfarcted area cells of water-treated hearts (MI/R) and of D-Arg-2'6'-Dmt-Lys-Phe-NH$_2$-treated hearts (MI/R+AP).

All data were normalized to β-actin and presented relative to the sham group.
Results qRT-PCR analysis showed that SERCA2a expression was decreased by 41% ($p<0.05$) in the MI/BZ group vs. sham. FIG. 1. Treatment with D-Arg-2'6'-Dmt-Lys-Phe-NH$_2$ restored SERCA2a expression to near normal levels in the MI/BZ+AP group. FIG. 1. There were no significant differences in the nonischemic remote area (MI/R).

These results show that aromatic-cationic peptides of the present technology, such as D-Arg-2'6'-Dmt-Lys-Phe-NH$_2$, or a pharmaceutically acceptable salt thereof, such as acetate or trifluoroacetate salt, are useful in the prevention and treatment of diseases and conditions associated with aberrant SERCA2a gene expression and/or levels. These results show that aromatic-cationic peptides of the present technology, such as D-Arg-2'6'-Dmt-Lys-Phe-NH$_2$, or a pharmaceutically acceptable salt thereof, such as acetate or trifluoroacetate salt, are useful in increasing SERCA2a gene expression levels and/or protein levels, and for treating or ameliorating the signs and symptoms of left ventricular remodeling.

Example 2

D-Arg-2'6'-Dmt-Lys-Phe-NH$_2$ Administered Post-Myocardial Infarction Improved LV Function This study demonstrates that chronic therapy with D-Arg-2'6'-Dmt-Lys-Phe-NH$_2$, begun at 2 hours post induction of heart failure by a transmural, non reperfused infarct in the rat, can improve outcome. Since D-Arg-2'6'-Dmt-Lys-Phe-NH$_2$ treatment started at two hours after permanent coronary occlusion, any benefit would be independent of phenomena such as no-reflow reduction. Two hours after coronary occlusion, all or nearly all cells destined to die due to ischemic necrosis have died in the rat model. This study measured the ability of D-Arg-2'6'-Dmt-Lys-Phe-NH$_2$ to reduce LV volumes, improve fractional shortening and ejection fraction, reduce infarct expansion, improve survival, improve hemodynamics, and reduce lung volumes.
Methods Rats were anesthetized, ventilated, and a thoracotomy performed in the left 4$^{th}$ intercostal space. Temperature was maintained at 36° C. by placing the rats on a heating pad during the procedure. The pericardium was excised and the proximal left coronary artery isolated and permanently occluded with a suture. Coronary artery occlusion was confirmed by cyanosis and akinesis of the anterior wall of the ventricle. The chest was closed, air evacuated, and the rats allowed to recover. Analgesia was administered per the veterinarian. An echocardiogram was obtained at approximately 15 minutes post coronary artery occlusion. At 2 hours rats were randomized to receive chronic daily D-Arg-2'6'-Dmt-Lys-Phe-NH$_2$ (delivered subcutaneously by an Alzet Osmotic Pump—3 mg/kg/day) or water. The Osmotic Pump delivered approximately 0.15 µl/hr for 6 weeks (model 2006; 200 µl). The Alzat pump was implanted subcutaneously between the shoulder blades while the rat was still anesthetized. After 6 weeks the rats were re-anesthetized, weighed, and a second echocardiogram was obtained under anesthesia. Cut downs were performed to isolate the carotid artery and jugular vein. Heart rate and blood pressure were measured. A Millar catheter was inserted into the left ventricle and LV systolic pressure, LV end diastolic pressure, +dP/dt, and −dP/dt were measured. A left ventriculogram was performed using IV fluoroscopic contrast in order to determine LV stroke volume and ejection fraction. Under deep anesthesia, the heart was excised, weighed, and pressure fixed at 11 mmHg with formalin. The lungs were also excised and weighed. Postmortem LV volume was measured by filling the LV cavity with fluid and measuring the total fluid. The hearts were sliced into four transverse sections and histologic slides were prepared and stained with hematoxylin and eosin and with picrosirius red, which stains collagen. Quantitative histologic analysis included: total circumference, scar circumference, non-infarcted wall circumference, total LV area, total LV cavity area, LV wall thickness (at several points), non-infarcted wall thickness; myocardial infarct expansion index.

Statistical Analysis

All data is reported as means±SEM. Values between groups were compared by Student t-test. P is significant at $p<0.05$ level.

Results

A total of 83 rats were involved in this study. Nine rats died within 2 hours after coronary occlusion (before treatment with D-Arg-2'6'-Dmt-Lys-Phe-NH or water). Seventy-four rats were randomized to receive D-Arg-2'6'-Dmt-Lys-Phe-NH$_2$ or water, and no rats died during the following 6 weeks treatment. Twenty rat hearts (10 in each group) were harvested for assessment of gene expression study. Fifty-four rats were used for assessment of cardiac function and post-infarct remodeling study.

LV Fractional Shortening by Echocardiography

Figure 2:
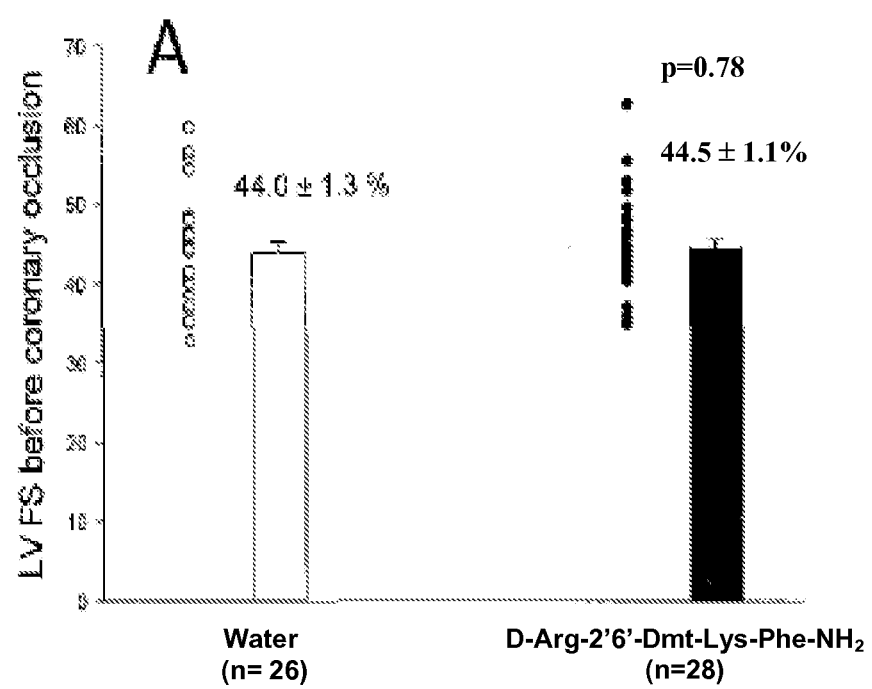
FIG. 2(A-C) are graphs showing the effect of D-Arg-2'6'-Dmt-Lys-Phe-NH$_2$ on left ventricle fractional shortening.
Figure 2:
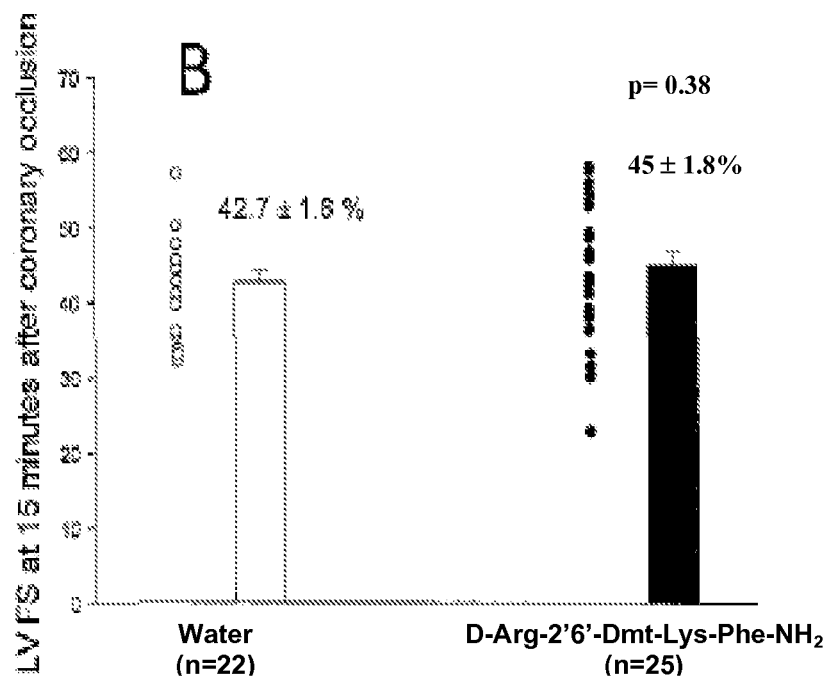
Figure 2:
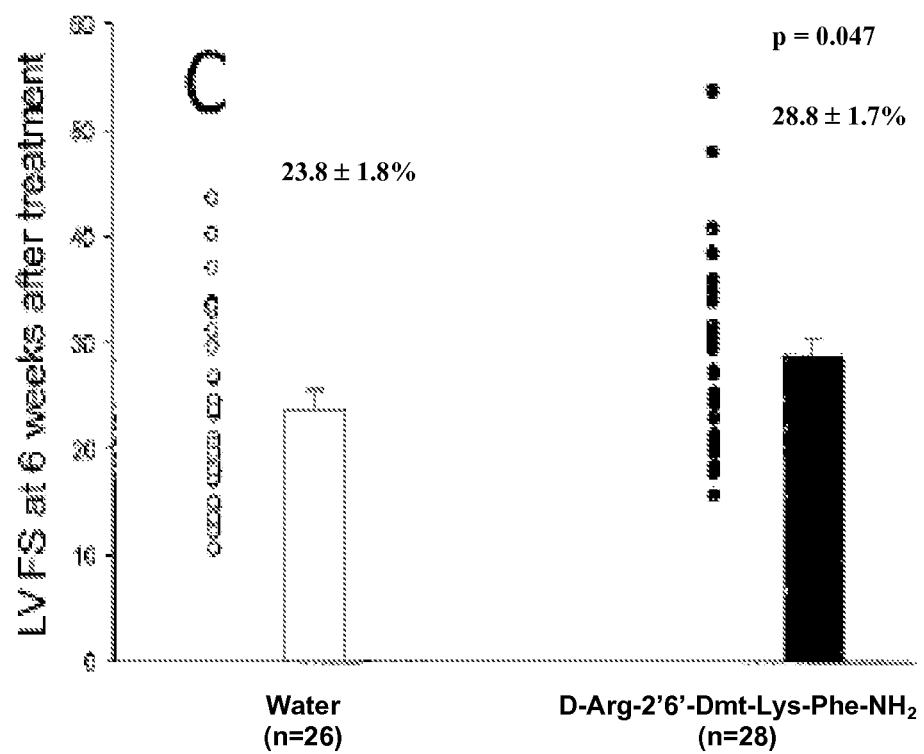

The left ventricular fractional shortening (LVFS) at baseline before coronary occlusion was similar between the water group (44.0±1.3%) and D-Arg-2'6'-Dmt-Lys-Phe-NH$_2$ group (44.5±1.1%, p=0.78) (FIG. 2A). At 15 minutes after coronary occlusion, LVFS remained similar between the 2 groups (42.7±1.6 in water group and 45±1.8 in D-Arg-2'6'-Dmt-Lys-Phe-NH$_2$ group, p=0.36) (LVFS did not decreased at 15 minutes probably because of hypercontractility in the non-ischemic myocardium) (FIG. 2B).

At 6 weeks after treatment, the LVFS fell versus baseline but was significantly higher in the D-Arg-2'6'-Dmt-Lys-Phe-NH$_2$ group (28.8±1.7%) than in the water group (23.8±1.8%, p=0.047) (FIG. 2C).

LV Stroke Volume and Ejection Fraction by LV Ventriculography

Figure 3:
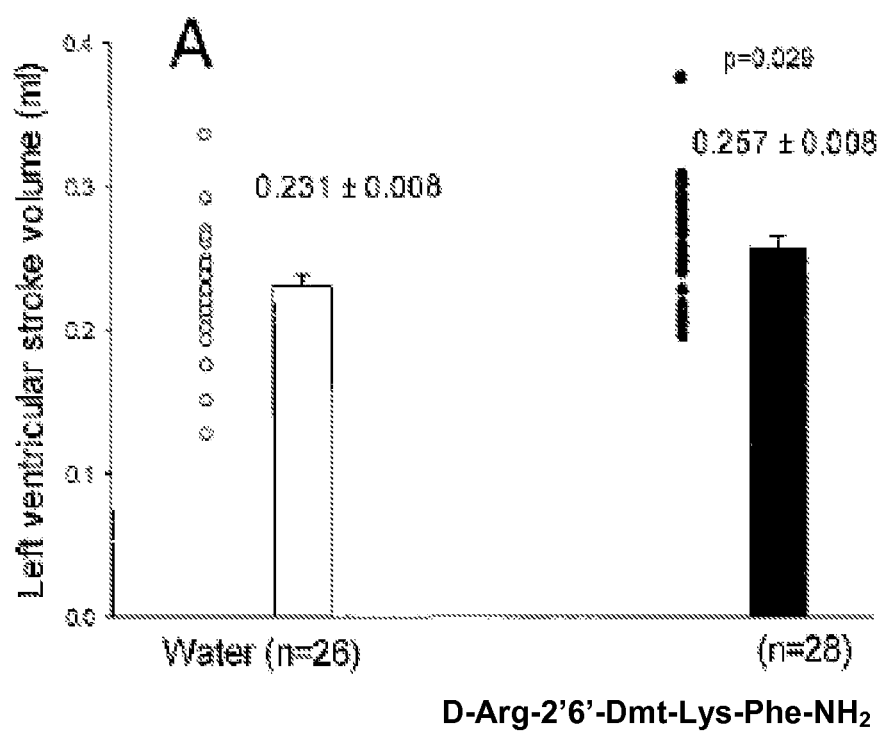
FIG. 3(A) is a graph showing the effect of D-Arg-2'6'-Dmt-Lys-Phe-NH$_2$ on left ventricle stroke volume.
FIG. 3(B) is a graph showing the effect of D-Arg-2'6'-Dmt-Lys-Phe-NH$_2$ on left ventricle ejection fraction.
Figure 3:
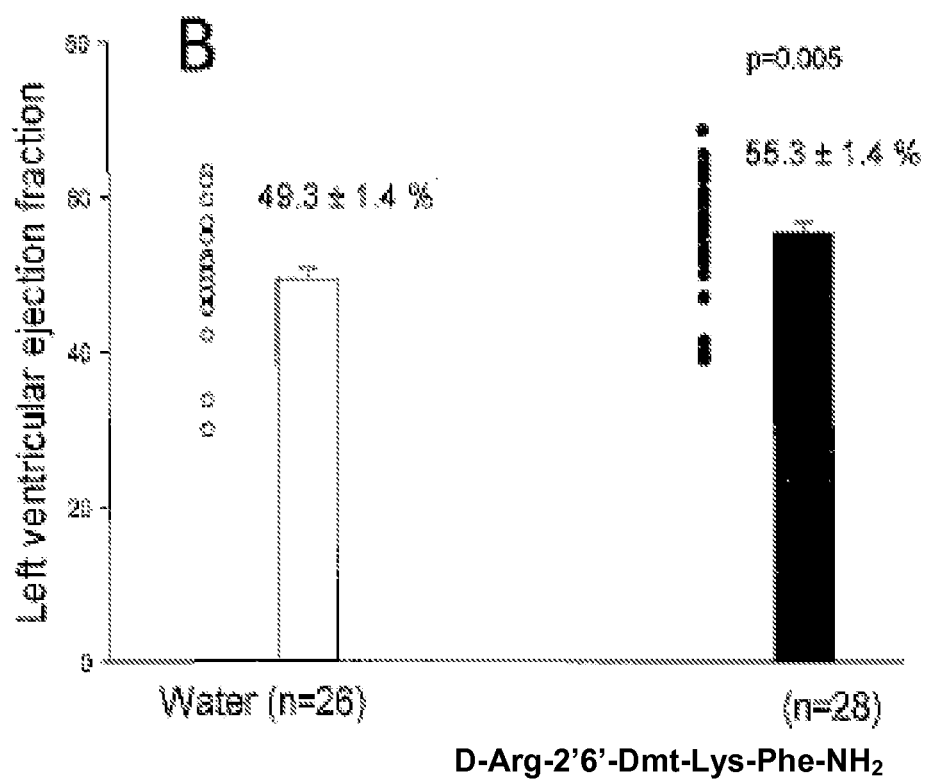

At 6 weeks after treatment, there was significantly higher LV stroke volume (0.257±0.008 ml) in the D-Arg-2'6'-Dmt-Lys-Phe-NH$_2$-treated group compared to the water group (0.231±0.008, p=0.029) (FIG. 3A). Additionally, there was a significantly higher LV ejection fraction (55.3±1.4%) in the D-Arg-2'6'-Dmt-Lys-Phe-NH$_2$-treated group compared to the water group (49.3±1.4%, p=0.005) (FIG. 3B).

Hemodynamics

No significant differences were noted in heart rate, systolic and diastolic blood pressure between the two groups at 6 weeks after treatment (Table 7). The LV positive/negative dp/dt, end systolic left ventricular pressure, end diastolic left ventricular pressure; Tau (Weiss) and Tau (Glantz) were comparable between the two groups (Table 8). There was a trend for lower minimum left ventricular pressure in the D-Arg-2'6'-Dmt-Lys-Phe-NH$_2$ group (0.64±0.55 mmHg) compared to water group (2.23±0.70 mmHg, p=0.082) (Table 8).

TABLE 7

Heart rate and blood pressure at 6 weeks after treatment

| Group | Heart Rate | Systolic BP (mmHg) | Diastolic BP (mmHg) | Mean BP (mmHg) |
|---|---|---|---|---|
| Water (n = 26) | 219 ± 6 | 124 ± 5 | 90 ± 3 | 101 ± 4 |
| D-Arg-2'6'-Dmt-Lys- Phe-NH$_2$ (n = 28) | 209 ± 5 | 114 ± 4 | 85 ± 2 | 94 ± 3 |
| t-test | 0.23 | 0.15 | 0.13 | 0.12 |

TABLE 8

Left ventricle hemodynamics at 6 weeks after treatment

| Group | +dp/dt | −dp/dt | Pes | Ped | Pmin | Tau Weiss | Tau Glantz |
|---|---|---|---|---|---|---|---|
| W | 5766 ± 268 | 3934 ± 184 | 113 + 5 | 7.82 ± 1.08 | 2.23 ± 0.70 | 15.2 + 0.4 | 23.6 ± 0.8 |
| P | 5668 ± 161 | 3639 ± 147 | 105 ± 3 | 5.63 ± 0.84 | 0.64 + 0.55 | 14.6 ± 0.6 | 24.6 ± 0.9 |
| t-test | 0.76 | 0.22 | 0.17 | 0.12 | 0.082 | 0.42 | 0.43 |

Figure 4:
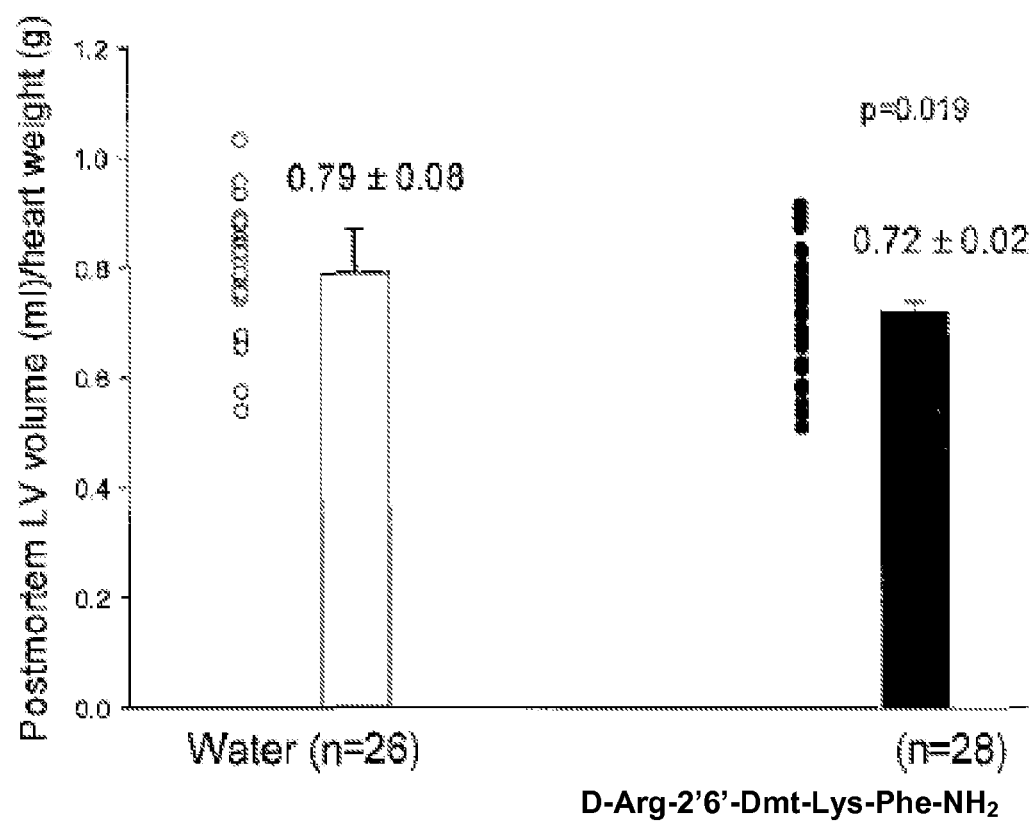
FIG. 4 is a graph showing the effect of D-Arg-2'6'-Dmt-Lys-Phe-NH$_2$ on post-mortem LV volume.

W = water (n = 26)
P = D-Arg-2'6'-Dmt-Lys-Phe-NH$_2$ (n = 28)
Post-mortem LV volumes There was a significant lower post-mortem LV volume in the D-Arg-2'6'-Dmt-Lys-Phe-NH$_2$-treated group compared to the water group when the LV volume standardized by heart weight (0.72±0.02 in D-Arg-2'6'-Dmt-Lys-Phe-NH$_2$ group vs 0.79±0.08 in water group; p=0.0019) (Table 9; FIG. 4).

TABLE 9

Heart weight and post-mortem LV volume

| Group | Heart weight (g) | LV volume (ml) | LV volume/heart weight |
|---|---|---|---|
| Water (n = 26) | 0.712 ± 0.064 | 0.561 ± 0.065 | 0.79 ± 0.08 |
| D-Arg-2'6'-Dmt-Lys-Phe-NH$_2$ (n = 28) | 0.724 ± 0.011 | 0.519 ± 0.019 | 0.72 ± 0.02 |
| t-test | 0.588 | 0.177 | 0.019 |

Scar Circumference, Scar Thickness, and Expansion Index

Figure 5:
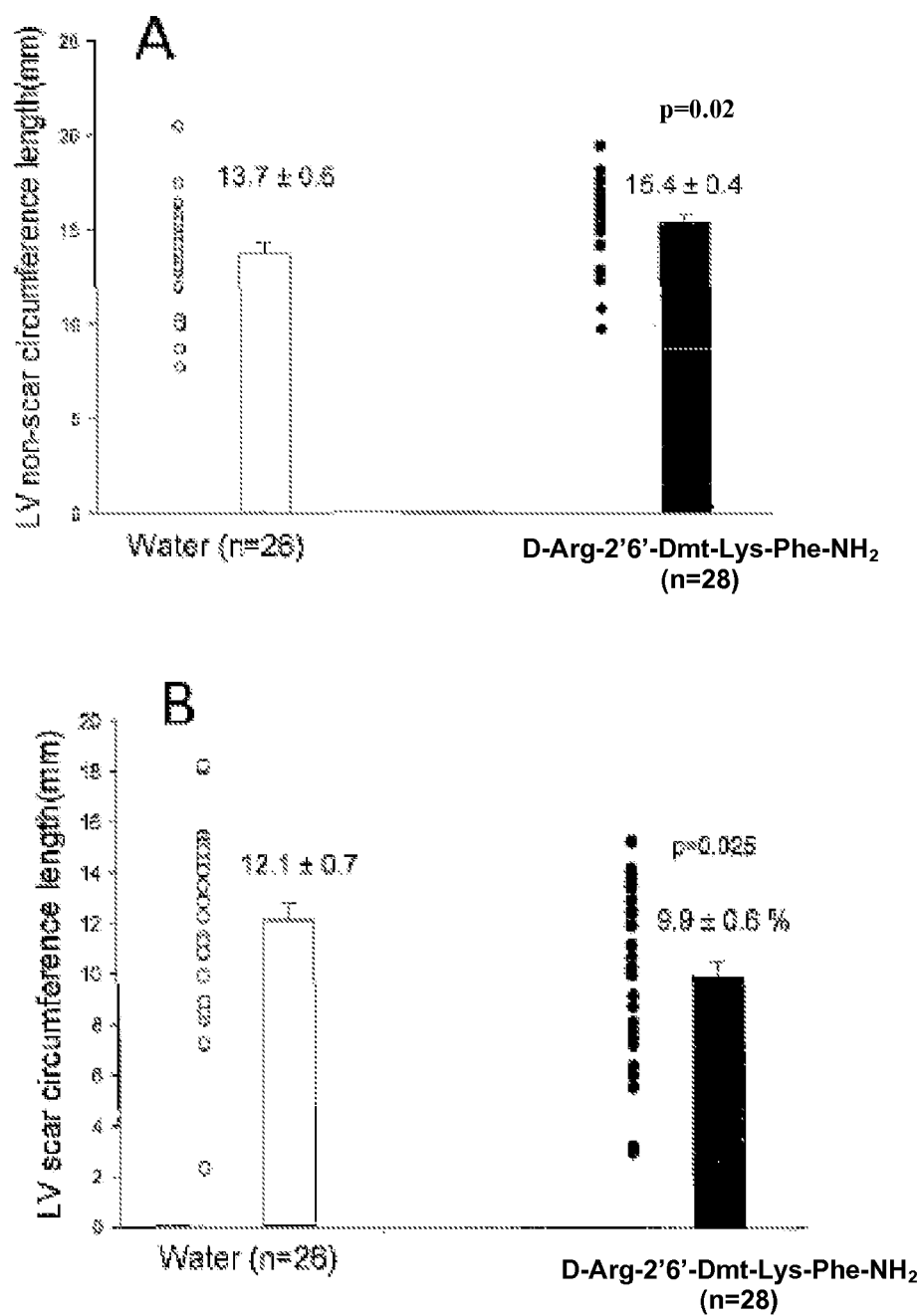
FIG. 5(A-C) are graphs showing the effect of D-Arg-2'6'-Dmt-Lys-Phe-NH$_2$ on LV non-scar and scar circumference.
Figure 5:
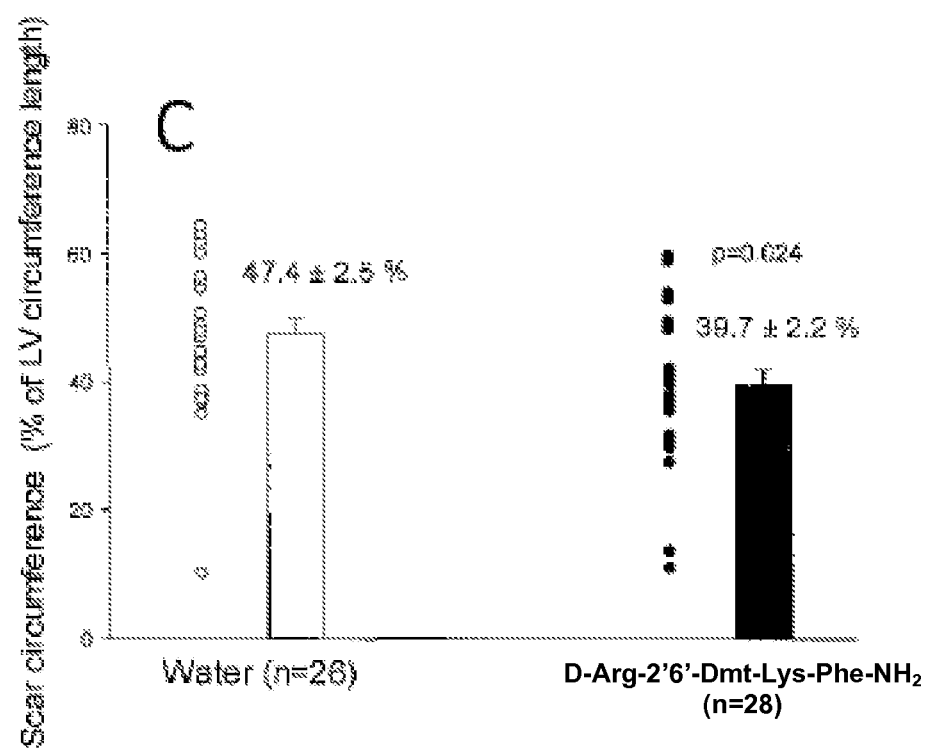

At 6 weeks after treatment, histological analysis revealed that the LV non-scar circumference was significantly longer in the D-Arg-2'6'-Dmt-Lys-Phe-NH$_2$ group (15.4±0.4 mm) compared to the water group (13.7±0.6 mm, p=0.02) (FIG. 5A). Additionally, the scar circumference was significantly smaller in the D-Arg-2'6'-Dmt-Lys-Phe-NH$_2$ group (9.9±0.6 mm) compared to the water group (12.1±0.7%, p=0.025) (FIG. 5B). The data also showed that the scar circumference, expressed as percentage of total LV circumference, was significantly smaller in the D-Arg-2'6'-Dmt-Lys-Phe-NH$_2$ group (39.7±2.2%) compared to the water group (47.4±0.03%, p=0.024) (Table 10; FIG. 5C). The scar thickness, septum thickness and expansion index expressed as: [LV cavity area/Total LV area×Septum thickness/Scar thickness], were comparable between the two groups (Table 10).

TABLE 10

Effects of D-Arg-2'6'-Dmt-Lys-Phe-NH$_2$ on scarring

| Group | Scar circumference (%) | Scar thickness (mm) | Septum thickness (mm) | Expansion index |
|---|---|---|---|---|
| Water (n = 26) | 47.4 ± 0.03 | 0.519 ± 0.019 | 1.43 ± 0.05 | 1.75 ± 0.09 |
| D-Arg-2'6'-Dmt-Lys-Phe-NH$_2$ (n = 28) | 39.7 ± 2.2 | 0.504 ± 0.039 | 1.45 ± 0.03 | 1.67 ± 0.12 |
| t-test | 0.024 | 0.37 | 0.68 | 0.57 |

Lung Weights (a Measure of Fluid Overload)

The lung dry and wet weight was measured, and the ratio of dry/wet was similar in the two groups.

The data demonstrated that chronic therapy with D-Arg-2'6'-Dmt-Lys-Phe-NH$_2$, begun at 2 hours post induction of myocardial infarction by ligation left coronary artery in the rat, improved cardiac function and prevented post-myocardial infarction remodeling at 6 weeks after treatment. D-Arg-2'6'-Dmt-Lys-Phe-NH$_2$ reduced scar circumference without increasing scar thickness, a phenomenon previously not observed with other therapies.

These results show that aromatic-cationic peptides of the present technology, such as D-Arg-2'6'-Dmt-Lys-Phe-NH$_2$, or a pharmaceutically acceptable salt thereof, such as acetate or trifluoroacetate salt, are useful in the prevention of LV remodeling and improvement of LV function. In particular, these results show that aromatic-cationic peptides of the present technology, such as D-Arg-2'6'-Dmt-Lys-Phe-NH$_2$, or a pharmaceutically acceptable salt thereof, such as acetate or trifluoroacetate salt, are useful to improve cardiac function post myocardial infarction, to prevent and/or ameliorate the characteristics, signs and symptoms of left ventricular remodeling, and to improve LV function.

Example 3

Effects of D-Arg-2'6'-Dmt-Lys-Phe-NH$_2$ on Post-Infarction Remodeling and Cardiac Function in a Rodent Model of Heart Failure In this study, D-Arg-2'6'-Dmt-Lys-Phe-NH$_2$ was tested to see if it would improve cardiac function and result in beneficial mitochondrial gene expression in a post-infarct model of heart failure.

Methods

Rats underwent the permanent coronary artery ligation, as described in Example 2. The rats were split into two groups and treated for six weeks with either 3 mg/kg/day of D-Arg-2'6'-Dmt-Lys-Phe-NH$_2$ or 0.9% NaCl (saline) continuously through mini-osmotic pumps, which were implanted into each animal.

After the six week period, LV function was assessed with echocardiography. Additionally, the hearts were excised and the heart tissue analyzed for LV chamber volume using tetrazolium salt staining Heart tissue in the border zone and remote areas around the infarct were also harvested and underwent gene array analysis to determine the expression levels of genes involved in mitochondrial metabolism.

Results

Figure 6:
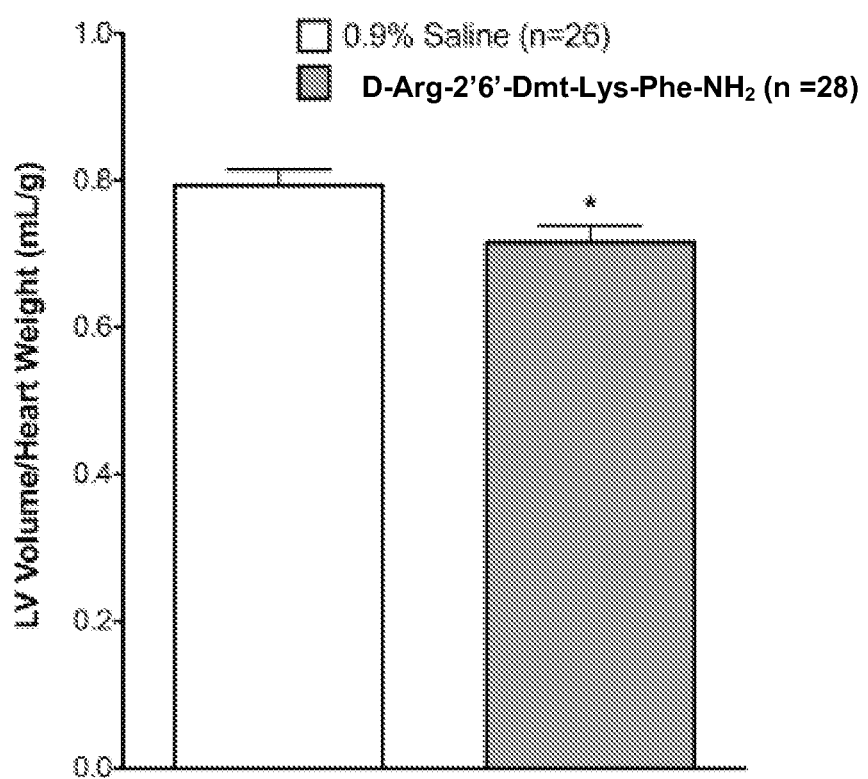
FIG. 6 is a graph showing that D-Arg-2'6'-Dmt-Lys-Phe-NH$_2$ reduces LV volume/heart weight.

FIG. 6 shows that treatment with D-Arg-2'6'-Dmt-Lys-Phe-NH$_2$ led to a decrease in LV volume/heart weight.

The data shows that chronic treatment with D-Arg-2'6'-Dmt-Lys-Phe-NH$_2$ reduced LV dilation in a post-infarction model of heart failure.

These results show that aromatic-cationic peptides of the present technology, such as D-Arg-2'6'-Dmt-Lys-Phe-NH$_2$, or a pharmaceutically acceptable salt thereof, such as acetate or trifluoroacetate salt, are useful in the prevention and treatment of diseases and conditions associated with heart failure and LV remodeling. In particular, these results show that aromatic-cationic peptides of the present technology, such as D-Arg-2'6'-Dmt-Lys-Phe-NH$_2$, or a pharmaceutically acceptable salt thereof, such as acetate or trifluoroacetate salt, are useful in decreasing or preventing an increase in LV volume/heart weight, and reduce LV dilation post myocardial infarction.

EQUIVALENTS

The present technology is not to be limited in terms of the particular embodiments described in this application, which are intended as single illustrations of individual aspects of the technology. Many modifications and variations of this technology can be made without departing from its spirit and scope, as will be apparent to those skilled in the art. Functionally equivalent methods and apparatuses within the scope of the technology, in addition to those enumerated herein, will be apparent to those skilled in the art from the foregoing descriptions. Such modifications and variations are intended to fall within the scope of the appended claims. The present technology is to be limited only by the terms of the appended claims, along with the full scope of equivalents to which such claims are entitled. It is to be understood that this technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

Other embodiments are set forth within the following claims.

What is claimed is:

1. A method for increasing sarco/endoplasmic reticulum Ca2+-ATPase 2a (SERCA2a) gene expression in a mammalian subject in need thereof, comprising administering to the mammalian subject a therapeutically effective amount of an aromatic-cationic peptide, wherein the aromatic-cationic peptide comprises D-Arg-2'6'-Dmt-Lys-Phe-NH$_2$, or a pharmaceutically acceptable salt thereof, wherein the subject has suffered a myocardial infarction.

2. The method of claim 1, wherein the myocardial infarction results from hypertension, ischemic heart disease, exposure to a cardiotoxic compound, myocarditis, thyroid disease, viral infection, gingivitis, drug abuse, alcohol abuse, pericarditis, atherosclerosis, vascular disease, hypertrophic cardiomyopathy, acute myocardial infarction, left ventricular systolic dysfunction, coronary bypass surgery, starvation, an eating disorder, or a genetic defect.

3. The method of claim 1, wherein the aromatic-cationic peptide is administered about 0.5 hours to 4 hours after the myocardial infarction.

4. The method of claim 1, wherein the increase of SERCA2a gene expression prevents, ameliorates, or treats left ventricular (LV) remodeling.

5. The method of claim 1, wherein the increase of SERCA2a gene expression increases LV function compared to a control subject not administered the aromatic-cationic peptide.

6. The method of claim 5, wherein increased LV function is determined by one or more physiological measures factors from the group consisting of reduced LV stroke volume, improved LV ejection fraction, improved fractional shortening, reduced infarct expansion, improved hemodynamics, and reduced lung volumes.

7. The method of claim 1, wherein the subject is a human.

8. The method of claim 1, wherein the peptide is administered orally, topically, systemically, intravenously, subcutaneously, intraperitoneally, or intramuscularly.

9. The method of claim 1, further comprising separately, sequentially or simultaneously administering a cardiovascular agent to the subject.

10. The method of claim 9, wherein the cardiovascular agent is selected from the group consisting of an anti-arrhthymia agent, a vasodilator, an anti-anginal agent, a corticosteroid, a cardioglycoside, a diuretic, a sedative, an angiotensin converting enzyme (ACE) inhibitor, an angiotensin II antagonist, a thrombolytic agent, a calcium channel blocker, a throboxane receptor antagonist, a radical scavenger, an anti-platelet drug, a β-adrenaline receptor blocking drug, α-receptor blocking drug, a sympathetic nerve inhibitor, digoxin, an inotrope, captopril, and an antihyperlipidemic drug.

* * * * *